(12) United States Patent
Welch et al.

(10) Patent No.: US 10,001,474 B2
(45) Date of Patent: Jun. 19, 2018

(54) FLUOROGENIC SEMICONDUCTOR NANOCRYSTALS

(75) Inventors: Eric Welch, Eugene, OR (US); David Bussian, Eugene, OR (US); Michael Ignatius, Eugene, OR (US); Lawrence Greenfield, Eugene, OR (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 212 days.

(21) Appl. No.: 14/124,354

(22) PCT Filed: Jun. 7, 2012

(86) PCT No.: PCT/US2012/041409
§ 371 (c)(1),
(2), (4) Date: Feb. 21, 2014

(87) PCT Pub. No.: WO2012/170727
PCT Pub. Date: Dec. 13, 2012

(65) Prior Publication Data
US 2014/0193841 A1    Jul. 10, 2014

Related U.S. Application Data

(60) Provisional application No. 61/494,255, filed on Jun. 7, 2011, provisional application No. 61/589,725, filed on Jan. 23, 2012.

(51) Int. Cl.
| | | |
|---|---|---|
| *G01N 33/52* | (2006.01) | |
| *G01N 33/58* | (2006.01) | |
| *C09K 11/08* | (2006.01) | |
| *B82Y 15/00* | (2011.01) | |

(52) U.S. Cl.
CPC ............ *G01N 33/525* (2013.01); *B82Y 15/00* (2013.01); *C09K 11/08* (2013.01); *G01N 33/581* (2013.01); *G01N 33/588* (2013.01)

(58) Field of Classification Search
CPC .............................. G01N 33/525; C09K 11/08
See application file for complete search history.

(56) References Cited

U.S. PATENT DOCUMENTS

| | | | |
|---|---|---|---|
| 6,528,675 B1 * | 3/2003 | Hammock | ............ C07C 255/37 |
| | | | 558/406 |
| 7,902,353 B2 | 3/2011 | Lu et al. | |
| 7,976,726 B2 | 7/2011 | Wang et al. | |
| 9,138,711 B2 * | 9/2015 | Treadway | .......... A61K 49/0067 |
| 2004/0146895 A1 | 7/2004 | Cook et al. | |
| 2008/0182333 A1 | 7/2008 | Bentley et al. | |
| 2009/0143239 A1 | 6/2009 | Lu et al. | |

(Continued)

FOREIGN PATENT DOCUMENTS

| | | |
|---|---|---|
| WO | WO 2010/039897 | 4/2010 |
| WO | WO-2010/039897 | 4/2010 |

OTHER PUBLICATIONS

Avwoghokoghene et al., "Isolation of Pure Cassava Linamarin as an Anti-Cancer Agen," published 2006.*

(Continued)

*Primary Examiner* — Tracy Vivlemore
*Assistant Examiner* — Nam P Nguyen

(57) ABSTRACT

Fluorogenic semiconductor nanocrystals and compositions thereof are provided herein, including kits, assay systems and methods for their preparation and use.

8 Claims, 16 Drawing Sheets

(56) References Cited

U.S. PATENT DOCUMENTS

| | | |
|---|---|---|
| 2010/0104476 A1 | 4/2010 | Ibanez et al. |
| 2010/0105082 A1 | 4/2010 | Ramadurai et al. |
| 2010/0151579 A1 | 6/2010 | Wang et al. |
| 2010/0184098 A1 | 7/2010 | Whateley |
| 2010/0200813 A1 | 8/2010 | Texier-Nogues et al. |
| 2014/0001436 A1* | 1/2014 | Welch .................... B82Y 30/00 257/14 |

OTHER PUBLICATIONS

Xu et al., "Quantum dot-based 'turn-on' fluorescent probe for detection of zinc and cadmium ions in aqueous media", vol. 687, p. 82-88, published Dec. 9, 2010.*

Merkoci et al., "A potentiometric biosensor for D-amygdalin based on a consolidated biocomposite membrane," vol. 391, pp. 65-72, published May 24, 1999.*

Chen et al., Luminescent CdS Quantum Dots as Selective Ion Probes, Anal. Chem., vol. 74, pp. 5132-5138, published Aug. 23, 2002.*

Wang et al., "Preparation of Highly Luminescent CdTe/CdS Core/Shell Quantum Dots", Chem. Phys. Chem., vol. 10, pp. 680-685, published Jan. 9, 2009.*

Agarwalla et al., "Fluorescent probes for the detection of cyanide ions in aqueous medium: cellular uptake and assay for b-glucosidase and hydroxynitrile lyase", J. Mater. Chem. B, vol. 3, pp. 9148-9156, published 2015.*

Touceda-Varela et al., "Selective turn-on fluorescence detection of cyanide in water using hydrophobic CdSe quantum dots", Chem. Commun. pp. 1998-2000, published Feb. 26, 2008.*

Shen et al., "High quality synthesis of monodisperse zinc-blende CdSe and CdSe/ZnS nanocrystals with a phosphine-free method", CrystEngComm., vol. 11, pp. 1733-1738, published 2009.*

PubChem-Hydrogen Cyanide, retrieved internet <https://pubchem.ncbi.nlm.nih.gov/compound/hydrogen_cyanide#section=Top>, printed retrieved on Aug. 15, 2017.*

Tatsuma et al., "Disposable test plates with tyrosinase and B-glucosidases for cyanide and cyanogenic glycosides", Analytica Chimica Acta, vol. 408, p. 233-240, published 2000.*

Kumar, Parveen et al., "Bioconjugation of InGaP quantum dots for molecular sensing", Anal. Biochem, 2011, 1-6.

Shang, Li et al., "Turn-on fluorescent cyanide sensor based on copper ion-modified CdTe quantum dots", Analyst, vol. 134, 2009, 107-113.

Wang, Qisui et al., "Conjugation and Fluorescence Quenching Between Bovine Serum Albumin", Protein & Peptides Letters, 18, 2011, 410-414.

Wang, Y et al., "A fluorescence Quenching Method for Determination of Copper Ions with CDTE Quantum Dots", J. Chil. Chem. Soc., 54, No. 3 (2009), 2009, 274-277.

EP12796955, "European Search Report dated Dec. 17, 2014", dated Dec. 17, 2014, 2 Pages.

Jin, W. et al., "Photoactivated luminescent CdSe quantum dots as sensitive cyanide probes in aqueous solutions", Chem. Commun., 2005, pp. 883-885.

Susumu, K. et al., "Enhancing the Stability and Biological Functionalities of Quantum Dots via Compact Multifunctional Ligands", Journal of the American Chemical Society, vol. 129, No. 45, Jul. 5, 2007, 13987-13996.

Valdes, M. G. et al., "Analytical nanotechnology for food analysis", Microchim Acta, vol. 166, May 12, 2009, 1-19.

* cited by examiner

FLUOROGENIC SEMICONDUCTOR NANOCRYSTALS

CROSS-REFERENCE TO RELATED APPLICATIONS

This application is a national phase entry under 35 U.S.C. § 371 of PCT/US2012/041409, filed on Jun. 7, 2012, which claims priority to U.S. Provisional Application No. 61/494,255, filed Jun. 7, 2011, and U.S. Provisional Application No. 61/589,725, filed Jan. 23, 2012, the disclosures of which are incorporated herein by reference in their entireties.

TECHNICAL FIELD

Fluorogenic semiconductor nanocrystals are provided that are useful in a variety of fields including biology, analytical and combinatorial chemistry, medical diagnostics, genetic and protein analysis and single molecule spectroscopy; also provided herein are compositions, kits and assay systems including fluorogenic semiconductor nanocrystals; and methods for their preparation and use.

BACKGROUND

Photoactive semiconductor nanocrystals are of interest for numerous optical and electronic applications. Semiconductor nanocrystals frequently include a semiconductor core and a passivating, semiconductor shell. Shell materials with bandgaps higher than those of the core materials can minimize deep-trap emission sites and can enhance quantum yield and stability of the nanocrystal particle. The optical properties and stability of a fluorescent nanocrystal can be compromised when in contact with metal atoms. In the presence of metals (e.g., metal ions or metal substrates), the intensity of fluorescence emission intensity of the semiconductor nanocrystals can be dramatically reduced. Once quenched, it is often impossible to regenerate the fluorescence emission of the nanocrystal. This sensitivity to metals severely limits the use of semiconductor nanocrystals in applications requiring contact with metal ions or metals (e.g., catalysts and metal substrates). Thus, there is a need to develop materials and methods for restoring the fluorescence intensity of quenched nanocrystals.

SUMMARY

Provided herein are fluorogenic semiconductor nanocrystals, kits and compositions including such nanocrystals, as well as methods of producing and using such nanocrystals. The nanocrystals described herein are useful in a variety of fields. These nanocrystals are ideally suited for biological and diagnostic applications but they also can be utilized in many other non-biological applications. Representative applications include, for example, analytical and combinatorial chemistry, medical diagnostics, and genetic and protein analysis. Due to their exceptional optical properties, these nanocrystals can function as powerful detection tools in a variety of life science applications ranging from cell and tissue staining (e.g., FISH), cell tracking, digital spectroscopy, immunoassays, Western blot detection of proteins, visualization of cell migration, single-molecule detection, flow cytometric analysis to in vivo imaging. The fluorogenic nanocrystals provided herein also can form foundational components in many types of electronic devices, such as LEDs, solar cells, transistors, and diode lasers and have numerous non-biological applications, such as sensors for inorganic compounds. Additionally, compositions and methods are provided that facilitate use of semiconductor nanocrystals in environments containing metals (e.g., metal substrates and metal catalysts). The nanocrystal compositions and methods provided herein overcome many of the disadvantages associated with conventional fluorescent semiconductor nanocrystals and provide new opportunities for the use of semiconductor nanocrystals previously not possible.

In one aspect, a nanocrystal is provided herein that includes a fluorescent semiconductor nanocrystal and a quencher group associated with the semiconductor nanocrystal. The fluorescent semiconductor nanocrystal in the absence of the quencher group has an initial fluorescence intensity ($F_0$), and the fluorogenic semiconductor nanocrystal has a quenched fluorescence intensity ($F_Q$), wherein $F_Q/F_0$ is less than about 1.0. In some embodiment, $F_Q/F_0$ is less than about 0.50. The fluorescent semiconductor nanocrystal can be non-emissive (i.e., $F_Q/F_0=0$) or substantially non-emissive (i.e., the nanocrystal may emit some light but below the detection threshold). The fluorescent semiconductor nanocrystal in the absence of the quencher group can emit light in the visible or near IR spectral range. A plurality of quencher groups can be associated with the nanocrystal (e.g., up to about 3000 quencher groups). In certain embodiments, greater than 50 quencher groups are associated with the nanocrystal. In certain embodiments, about 50 to about to about 3000; or about 50 to about 1000; or about 1000 to about 2000; or about 2000 to about 3000 quencher groups are associated with the nanocrystal.

In another aspect, a population of fluorogenic nanocrystals is provided that comprises a plurality of fluorogenic semiconductor nanocrystals as described herein. The quantum yield of the population of fluorogenic nanocrystals in the absence of the plurality of quencher groups can be greater than about 10%; or about 25%; or about 50%; or about 75%.

In yet another aspect, a composition is provided that includes a population of fluorogenic semiconductor nanocrystals as described herein and an aqueous or organic medium or a solid support, wherein the nanocrystal is associated with the solid support, if present. The composition can be formulated for use in an in vitro or in vivo biological assay. In certain embodiments, the population of nanocrystals is dispersed in an organic medium. In other embodiments, composition is a stable dispersion of fluorogenic semiconductor nanocrystals (non-aggregated) in an aqueous medium. In certain embodiments, the composition includes less than $3.0 \times 10^7$ M of quencher groups. The composition can further include an activator as described herein in an amount sufficient to activate the fluorescence emission of the fluorescent nanocrystal (e.g., such that $F_A/F_Q$ is 10:1 or greater). In yet another aspect, methods for producing a fluorogenic nanocrystal or population thereof is provided. A representative method is provided that includes a) providing a reaction mixture including a fluorescent semiconductor nanocrystal and at least one solvent; and b) adding to the reaction mixture a quencher group (or a plurality of quencher groups) in an amount sufficient to reduce the fluorescence emission of the semiconductor nanocrystal. The fluorescence emission signal can be reduced by at least 50% upon addition of the quencher group. The fluorescent semiconductor nanocrystal in the absence of the quencher group can have an initial fluorescence intensity ($F_0$), and the fluorogenic semiconductor nanocrystal can have a quenched fluorescence intensity ($F_Q$), wherein $F_Q/F_0$ is less than about 0.50. Typically, $10^{-8}$ M to about $1^{0-3}$ M of quencher groups is present in the reaction mixture. In certain embodiments, the method further includes adding to the reaction mixture greater than 50 quencher groups per nanocrystal (i.e., quencher group to nanocrystal ratio is 50:1 or greater). In certain embodiments, this ratio is about 50 to about 3000; or about 50 to about 1000; or about 1000 to about 2000; or about 2000 to about 3000.

In certain methods, the fluorescent semiconductor nanocrystals are water-dispersible. Alternatively, the hydrophobic nanocrystals can be used. In some embodiments, the method can further include treating the semiconductor nanocrystal after addition of the quenching group with a hydrophilic compound that renders the nanocrystal water-dispersible. Certain methods further include attaching to the nanocrystal with an organic molecule (e.g., biomolecule).

In yet another aspect, a population of fluorogenic nanocrystals is provided, wherein the nanocrystals are produced according to any of the methods described herein.

Also provided herein are kits and methods of using populations of nanocrystals. Thus, in yet another aspect, a kit for activation of quenched semiconductor nanocrystals is provided. An exemplary kits includes a) a population of fluorogenic nanocrystals as described herein; and b) an activator. The kit can further include a cyanogenic substrate that can release a cyanide or isonitrile source. The kit can further include a cyanogenic enzyme that is capable of cleaving the cyanogenic substrate to release a compound comprising a cyanide ion or an isonitrile group.

Thus, in another aspect, a kit is provided that includes a) a population of fluorogenic nanocrystals as disclosed herein; b) a cyanogenic enzyme; and c) a cyanogenic substrate. In yet another aspect is provided a kit that includes a) a population of fluorescent nanocrystals; b) a copper source; c) a cyanogenic enzyme; and d) a cyanogenic substrate. The cyanogenic enzyme can be associated with an antibody or solid support (e.g., slide, microchip, bead, fiber, microwell plate, nanowell, magnetic disk, or magnetic tape). In certain kits, each nanocrystal in the population of nanocrystals can be associated with a first binding group (e.g., antibody), and the cyanogenic enzyme is associated with a second binding group (e.g., antibody), wherein the first and second binding groups are different.

In another aspect, kits for conducting click cycloaddition reactions are provided. An exemplary kit includes a) a population of fluorescent semiconductor nanocrystals, wherein the semiconductor nanocrystals each include an alkyne reactive group or an azide reactive group; b) a copper source (Cu(I) or Cu(II) ion); and c) at least one activator.

In any of the kits provided herein, the population of nanocrystals can be suspended in an aqueous medium or associated with a solid support or antibody. Certain kits utilize two or more different populations of nanocrystals.

In yet another aspect, methods for activating a fluorogenic semiconductor nanocrystal are provided. A representative includes: a) providing a fluorogenic semiconductor nanocrystal as described herein; and b) contacting the nanocrystal with an activator, wherein the fluorescence intensity of the fluorogenic semiconductor nanocrystal after contact with the activator increases. In some embodiments, the nanocrystal is contacted with the activator at a pH of 7 greater. The nanocrystal after contact with the activator can have an activated fluorescence intensity ($F_A$), wherein $F_A/F_Q$ is greater than 1. In certain methods, $F_A/F_Q$ is 10 or greater. In certain methods, the quencher compound can be desorbed from the nanocrystal surface upon contact with the activator.

Certain methods further include contacting the nanocrystal with a cyanogenic substrate capable of releasing an isonitrile or a cyanide group. Certain methods further include hydrolyzing the substrate to release a cyanide ion. The substrate can be a cyanogenic enzyme substrate (e.g., cyanogenic glucoside). Examples of substrates for use in the disclosed methods include amygdalin, prunasin, dhurrin, vicianin, linamarin, lotaustralin, cyanohydrins, cyanohydrin esters, cyanohydrin amides, acetone cyanohydrins, mandelonitrile, and acyl cyanides.

Certain methods further include contacting the cyanogenic enzyme substrate with a cyanogenic enzyme capable of cleaving the cyanogenic substrate to release a compound comprising an isonitrile group or a cyanide group. The cyanogenic enzyme can be a glucosidase. For example, the cyanogenic enzyme can be almond β-glucosidase, amygdalase, and linamarase. Certain methods further include contacting the cyanogenic enzyme substrate with a lysase (e.g., α-hydroxynitrile lysase), esterase, protease, or galactase. Certain methods further include contacting the fluorogenic nanocrystal with a metal chelator (e.g., EDTA).

Also provided is a population of activated fluorogenic nanocrystals produced according to any one of the methods disclosed herein. The quantum yield of the population of activated fluorogenic nanocrystals can be greater than about 10%; or about 25%; or about 50%; or about 75%.

Also provided herein are methods of using the disclosed fluorogenic nanocrystals. For example, methods are provided for detecting the presence of an analyte (e.g., biomolecule, cell, or a small inorganic or organic molecule) in a sample. Examples of biomolecules that can be detected using the methods provided herein include proteins, peptides, nucleic acids, oligonucleotides, aptamers, lipoproteins, glycoproteins, carbohydrates, lipids, phospholipids, aminoglycans, enzymes, and antigens. In certain embodiments, the analyte is a post-translationally modified protein (e.g., phosphorylated, glycosylated, and the like). Representative inorganic or organic molecules that can be detected using the disclosed methods include, e.g., drugs, toxins, and metal ions.

A representative method includes a) providing a cyanogenic substrate capable of releasing a cyanide source (e.g., cyanide ion or isonitrile group); b) contacting the sample with a fluorogenic semiconductor nanocrystal as disclosed herein, wherein the nanocrystal is associated with a first binding group; c) contacting the sample with a second binding group, wherein the second binding group is associated with a cyanogenic enzyme, wherein the first and second binding groups are different, and wherein the first and second binding groups bind to the analyte, if present; d) contacting the cyanogenic enzyme with the cyanogenic substrate, thereby releasing the cyanide source from the cyanogenic substrate; and e) detecting fluorescence emission of the fluorogenic semiconductor nanocrystal, wherein an increase in the intensity of fluorescence emission signal indicates the presence of the analyte in the sample.

Also provided is a method of detecting the presence of an analyte in a sample that includes a) providing i) a cyanogenic substrate that is capable of releasing a cyanide source (e.g., cyanide ion or an isonitrile group) and ii) a fluorogenic nanocrystal as described herein; b) contacting the sample with a binding group and a second binding group, wherein the first binding group and the second binding group are different, wherein the first and second binding groups bind to the analyte, if present, wherein the first binding group is associated with a cyanogenic enzyme; c) contacting the cyanogenic enzyme with the cyanogenic substrate to release the cyanide source in the presence of the nanocrystal; and d) detecting fluorescence emission of the fluorogenic semiconductor nanocrystal, wherein an increase in the intensity of fluorescence emission signal indicates the presence of the analyte in the sample. The first binding group can be associated with a third binding group, wherein the third binding group is associated with the cyanogenic enzyme. Optionally, the second binding group can be associated with the analyte indirectly via a third binding group Also provided is a method of detecting the presence of an analyte in a sample that includes a) providing a solid support, wherein the support is associated with a first binding group and a cyanogenic enzyme; b) contacting the solid support with the sample and a second binding group wherein the first and second binding group binds to the analyte, if present, wherein the second binding group is associated with the fluorogenic semiconductor nanocrystal of claim 1 and wherein the first and second binding groups are different; c) contacting the cyanogenic enzyme with a cyanogenic substrate to release a cyanide source (e.g., cyanide ion or isonitrile group); and d) detecting fluorescence emission of the fluorogenic semiconductor nanocrystal, wherein an increase in the intensity of fluorescence emission signal indicates the presence of the analyte in the sample. Optionally, the second binding group can be associated with the analyte indirectly via a third binding group In any of the methods provided herein, the first, second and/or third binding group, if present, can be an antibody, oligonucleotide, aptamer, or a chemical binding group. Chemical binding groups include, for example, polymers, metal ligands, protein binders, and the like). In certain embodiments, first binding group is associated with a solid support, and, the method optionally further includes washing the solid support before addition of the cyanogenic substrate.

In yet another aspect, methods of detecting the presence of a nucleic acid in a sample are provided. A representative method includes a) contacting a sample with a fluorogenic semiconductor nanocrystal as described herein, wherein the nanocrystal is associated with a first nucleic acid having a known sequence; b) contacting the sample with a second nucleic acid having a known sequence, wherein the second nucleic acid is associated with a cyanogenic enzyme; c) contacting the cyanogenic enzyme with the cyanogenic substrate, thereby releasing a cyanide source (e.g., cyanide ion or isonitrile group) from the cyanogenic substrate; and e) detecting the fluorescence emission of the fluorogenic semiconductor nanocrystal, wherein an increase in the intensity of fluorescence emission signal indicates the presence of a nucleic acid strand having a sequence capable of hybridizing to the first and second nucleic acid strands.

In yet another aspect, a method of activating a semiconductor nanocrystal is provided that includes a) providing at least one fluorescent semiconductor nanocrystal or fluorogenic nanocrystal as disclosed herein; b) contacting the semiconductor nanocrystal with a compound to modulate the at least one optical property of the nanocrystal; and c) determining the position of the nanocrystal. In certain methods, the position of the nanocrystal can determined by imaging. The positions of a first nanocrystal and a second nanocrystal can be determined to an accuracy that is less than the wavelength of the light emitted by first and/or second nanocrystal.

In yet another aspect, a method of detecting cyanide ions in a sample is provided that includes a) providing a sample; b) contacting the sample with a fluorogenic semiconductor nanocrystal as disclosed herein, wherein the quencher group is capable of complexing with a cyanide ion; and c) detecting fluorescence emission of the nanocrystal, wherein an increase in the intensity of fluorescence emission signal indicates the presence of the cyanide ions in the sample.

In yet another aspect, methods of enhancing the brightness of a semiconductor nanocrystal are provided. A representative method includes a) providing a fluorescent semiconductor nanocrystal; and b) contacting the nanocrystal with an activator, such that the intensity of the fluorescence emission of the population of nanocrystals increases by at least 10%.

In yet another aspect, methods of attaching a compound to a semiconductor nanocrystal are provided. A representative method includes a) contacting a fluorescent semiconductor nanocrystal that comprises an alkyne reactive group or an azide reactive group; b) contacting the nanocrystal with a reactive material comprising a group capable of reacting with the alkyne reactive group or azide reactive group of the compound in the presence of Cu(I) or Cu(II) ions; and c) contacting the nanocrystal with an activator, wherein the fluorescence emission intensity of the nanocrystal increases upon contact with the activator. In certain embodiments, the nanocrystal is a fluorogenic semiconductor as disclosed herein. Certain methods further include contacting the nanocrystal with the reactive material in the presence of at least one reducing agent. The reactive material can include a molecule selected from the group consisting of an amino acid, a peptide, a protein (e.g., enzyme or an antibody), a carbohydrate, a polysaccharide, a nucleoside, a nucleotide, an oligonucleotide, a nucleic acid polymer, a drug, a lipid, and a synthetic polymer. The reactive material can be associated with a solid support (either covalently or non-covalently). Certain methods further include monitoring the fluorescence emission intensity of the nanocrystal, wherein the emission intensity increases by at least 10% upon addition of the activator.

Also provided herein are fluorogenic assay systems. A representative fluorogenic assay system provided herein includes a) a fluorogenic semiconductor nanocrystal as disclosed herein, wherein the nanocrystal is associated with a first binding group; b) a cyanogenic enzyme associated with a second binding group, wherein the second binding group is different from the binding group, and wherein the first and the second binding groups are associated with an analyte; and c) a cyanogenic substrate capable of releasing a cyanide source (e.g., cyanide ion or an isonitrile group) upon contact with the cyanogenic enzyme. The cyanogenic enzyme and/or the second binding groups in the assay system can be associated with a solid support.

In yet another aspect, a method of identifying a cell or cellular component in a sample is provided. A general method for identifying a cell or cellular component includes a) contacting a cell or cellular component in the sample with a fluorogenic semiconductor nanocrystal as described herein under conditions in which the nanocrystal is transported across the cell membrane to provide a labeled cell or cellular component; b) exposing the labeled cell or cellular component to an excitation energy source to activate the semiconductor nanocrystal, such that the activated nanocrystal has a fluorescence intensity ($F_A$), wherein $F_A/F_Q$ is greater than 1; and c) detecting the fluorescence emission of the activated nanocrystal, thereby identifying the cell or cellular component in the sample.

In yet another aspect, a method of identifying a cell in a mixed population of cells is provided that includes: a) contacting a first cell with a fluorogenic semiconductor nanocrystal as described herein under conditions in which the nanocrystal is associated with the cell to provide a first labeled cell (e.g., the nanocrystal can be transported across the cell membrane, associated with the cell membrane or can be endocytosed into the cell); b) mixing the first labeled cell with a second cell distinct from the first cell to form a mixed population of cells; c) culturing the mixed population of cells; d) exposing the labeled cell to an excitation energy source to activate the semiconductor nanocrystal, such that the activated nanocrystal has a fluorescence intensity ($F_A$), wherein $F_A/F_Q$ is greater than 1; and f) detecting the fluorescence emission of the activated nanocrystal, thereby identifying the first labeled cell in the mixed population of cells. The method further can include contacting the labeled cell or cellular component to an activator prior to or during exposing the labeled cell or cellular component to the excitation energy source.

The methods provided herein can be implemented to identify any type of cell, including, but not limited to a mammalian or yeast cell. In some embodiments, the cell a live cell.

In yet another aspect, a method for detecting a fluorogenic nanocrystal is provided that includes: a) placing a fluorogenic nanocrystal as described herein onto the surface of a photonic crystal sensor; b) illuminating the photonic crystal sensor with light, thereby causing the sensor to exhibit an extraction resonance mode having a spectrum which at least partially overlaps the emission spectrum of the fluorogenic nanocrystal, wherein the illumination and the extraction resonance mode activates the fluorogenic nanocrystal, such that the activated nanocrystal has a fluorescence intensity ($F_A$), wherein $F_A/F_Q$ is greater than 1; and c) detecting the emitted light from the activated nanocrystal, thereby detecting the fluorogenic nanocrystal. The method further can include contacting the fluorogenic nanocrystal with an activator, thereby increasing the rate of activation and/or fluorescence intensity.

In any of the compositions, kits, systems or methods provided herein, the fluorogenic nanocrystal can include a semiconductor core and an external semiconductor shell layer disposed on the semiconductor core. The nanocrystal core and/or shell layer, if present, can include a Group II-VI, a Group II-VI-VI, Group II-II-VI, or Group III-V semiconductor material. For example, in certain embodiments, the core includes CdSe. The shell layer can include a semiconductor material selected from CdZnS, ZnS, CdS, CdSeS, ZnSeS, CdZnSeS, ZnSe, and combinations thereof.

In any of the compositions, kits, systems or methods provided herein, the semiconductor nanocrystal can be hydrophobic or water-dispersible. For example, the nanocrystal can further include a hydrophilic layer on the surface of the semiconductor nanocrystal that renders the nanocrystal water-dispersible. The nanocrystal can further include a biomolecule linked to the semiconductor nanocrystal or hydrophilic layer (e.g., a nucleotide, oligonucleotide, a nucleic acid polymer, an amino acid, polypeptide, a protein, a polysaccharide, a lipid, and biotin).

In any of the compositions, kits, systems or methods provided herein, the quencher group can be a metal source. A metal source can be any compound that contains or is capable of providing a metal atom. The metal source can be or include a metal atom, metal ion, metal salt, or a metal-containing compound. For example, the quencher group can be or include a transition or non-transition metal ion. The quencher group can be or include a metal ion selected from Cu(I), Cu(II), Ag (I), Hg (I,II), Pb (II), Pb(IV), Fe (II), Fe(III), Co (II), Ni (II), and Cr (I, II, III, IV, V, or VI). The quencher group can be an anion such as $S^{2-}$, $Se^{2-}$, $F^-$, $Cl^-$, $Br^-$, $I^-$, $Te^{2-}$, $As^{3-}$, or phosphonate. In some embodiments, the quencher group is or comprises a metal salt. The quencher group can be an organic ligand that includes a thiol or thiolate group. In certain embodiments, the quencher is dihydrolipoic acid (DHLA). In certain embodiments, the quencher group is a copper source. A copper source can be any compound that provides a copper atom. The copper source can be a copper ion, such as, for example, Cu(I) or Cu(II)). In other embodiments, the quencher compound is not a Cu (II) ion.

In any of the compositions, kits, systems or methods provided herein, the activator can be a reducing agent, and oxidizing agent, proton or metal ion binding compound. In some embodiments, the activator is a metal chelating agent. Exemplary activators can be selected from cyanide, nitrile, isonitrile, azide, thiocyanate, amine, imidazole, thiolate, carboxylate, NO, CO, halides (e.g. fluoride), peroxide, reactive oxygen scavenger (ROS), and hydroxide. In certain embodiments, the activator includes a cyanide, isonitrile or nitrile source. For example, the cyanide source can be a cyanide ion, cyanide salt or an organocyanide compound). In certain compositions, kits, systems or methods provided herein, the activator is a protein (e.g., fetal bovine serum, bovine serum albumin, casein, goat serum, fish serum and the like) or a polymer (e.g., polyethyleneimine, polypeptide, polyethylene glycol, polyacrylic acid or a derivative thereof).

These and other features, aspects, and embodiments are described herein.

BRIEF DESCRIPTION OF THE DRAWINGS

For a more complete understanding of the principles disclosed herein, and the advantages thereof, reference is now made to the following descriptions taken in conjunction with the accompanying drawings, in which.

DETAILED DESCRIPTION

Figure 1:
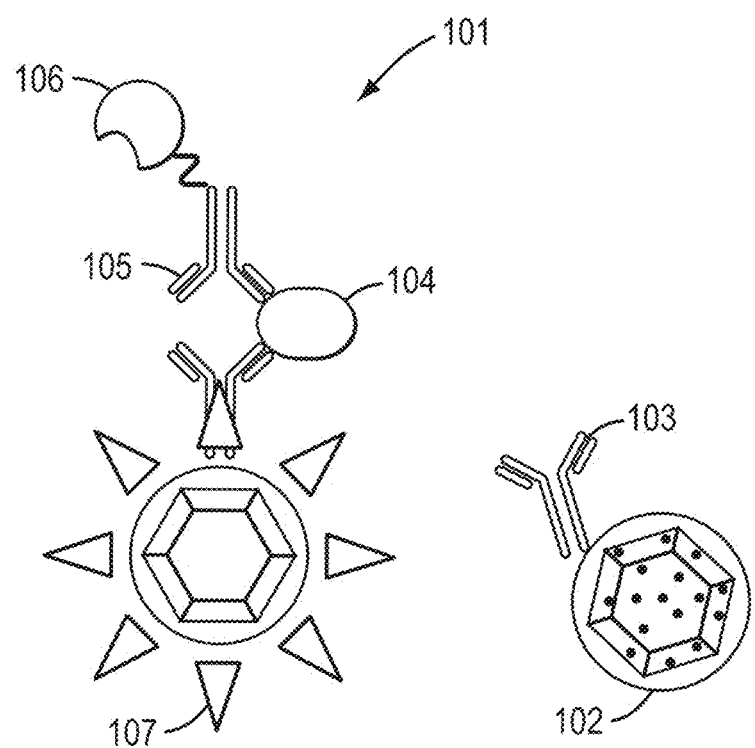
FIG. 1 illustrates a homogeneous proximity assay using a fluorogenic nanocrystal as disclosed herein.

The embodiments described herein may be understood more readily by reference to the following detailed description of the embodiments and the Examples included herein. It is to be understood that the terminology used herein is for the purpose of describing specific embodiments only and is not intended to be limiting.

The entirety of each patent, patent application, publication and document referenced in this disclosure is hereby incorporated by reference in its entirety, including all tables, drawings, and figures.

Unless defined otherwise, all technical and scientific terms used herein have the same meaning as is commonly understood by one of ordinary skill in the art.

As used herein, "a" or "an" means "at least one" or "one or more.

As used herein, "about" means that the numerical value is approximate and small variations would not significantly affect the use and practice of the compositions and methods provided herein. Where a numerical limitation is used, unless indicated otherwise by the context, "about" means the numerical value can vary by ±10% and remain within the scope of the disclosed embodiments.

"Nanocrystal" as used herein refers to a particle with at least one major dimension in the nanosize range (about 1 nm to about 1000 nm in its largest dimension) and formed of an inorganic substance that has an ordered crystalline structure. A nanocrystal can be made from a material that in the bulk is a semiconductor or insulating material and which has a tunable photophysical property in the near ultraviolet (UV) to far infrared (IR) range. A nanocrystal made from such a material is referred to herein as a "semiconductor nanocrystal." A nanocrystal can include a core that is made of a crystalline material, such as a semiconductor material, and the nanocrystal core can be surrounded by one or more external shell layers formed of one or more types of insulating or semiconductor materials. A semiconductor nanocrystal to which no shell has been applied is referred to herein as a "core nanocrystal" or "semiconductor core nanocrystal," whereas a semiconductor nanocrystal core with a semiconductor shell is referred to herein as a "core/shell nanocrystal" or "semiconductor core/shell nanocrystal." A nanocrystal, such as a core or core/shell nanocrystal, can be associated with an organic coating or ligands or other material on the surface of the particle, e.g., trioctylphosphine (TOP), trioctylphosphine oxide (TOPO), oleic acid, octylphosphonic acid (OPA), ethylphosphonic acid (EPA), tetradecylphosphonic acid (TDPA), or other material that is not readily removed from the surface by ordinary solvation. In certain embodiments, the organic coating or a layer of ligands on the particle surface is cross-linked. These surface coatings or layers can modify the properties of the particle, for example, increasing or decreasing solubility in water or other solvents.

"Water-soluble" or "water-dispersible" is used herein to mean the item can be soluble or does not agglomerate in aqueous conditions, such as in water or water-based solutions or buffer solutions, including those used in biological or molecular detection systems as known by those skilled in the art. While water-soluble nanocrystals are not truly 'dissolved' in the sense that term is used to describe individually solvated small molecules, they are solvated (e.g., via hydrogen, electrostatic or other suitable physical/chemical bonding) and suspended in solvents that are compatible with their outer surface layer, thus a nanocrystal that is readily dispersed in water is considered water-soluble or water-dispersible. A water-soluble nanocrystal can also be considered hydrophilic, since its surface is compatible with water and with water solubility.

"Population" as used herein refers to a plurality of nanocrystals, where the nanocrystals can have similar physical and/or optical properties. "Population" can refer to a solution or structure with more than one nanocrystal, In certain embodiments, the nanocrystals in the solution or structure are at a concentration suitable for single molecule analysis.

"Fluorogenic" as used herein refers to process in which fluorescent signal is generated or enhanced. The term also refers to a chemical, electrochemical, or photochemical reaction that transforms weakly or non-fluorescent groups into fluorescent groups. In the context of analytical assays, the amount of fluorescence can be quantitated and correlated with the amount of analyte.

"Fluorogenic nanocrystal" or "fluorogenic semiconductor nanocrystal" as used herein refers to a semiconductor nanocrystal whose fluorescence properties can be modulated via a chemical reaction or irradiation. A fluorescent nanocrystal that exhibits some detectable fluorescence and is capable of exhibiting an enhancement in an optical property (e.g., emission intensity or quantum yield) is also referred to herein as a "fluorogenic nanocrystal."

"Fluorogenic substrate" as used herein refers to a non-fluorescent material that is acted upon by another compound to produce a fluorescent compound or a compound that can activate or enhance the fluorescence of another compound (e.g., a semiconductor nanocrystal). A fluorogenic substrate can produce a species (referred to herein as an "activator") that can activate (e.g., "turn on") or enhance an optical property of another compound. In certain cases, the activator can undergo a further reaction to generate or release the activating species. A fluorogenic substrate that can be acted on by a specific enzyme is referred to herein as a "fluorogenic enzyme substrate." A fluorogenic substrate that can be cleaved to release a cyanide source (e.g., cyanide ion or organocyanide compound) is referred to herein as a "cyanogenic substrate." Where cleavage can be achieved by an enzyme, the fluorogenic substrate also can be referred to as a "cyanogenic enzyme substrate."

A "quencher" as used herein refers to a compound or group that can transform an emissive semiconductor nanocrystal into an optically inactive species in the region of the spectrum where the emissive nanocrystal emits prior to treatment with the quencher. The interaction between the nanocrystal and the quencher can be permanent or transient and can reduce an optical property to varying degrees. A quencher can be a chemical group (or a plurality of groups), in which case the quencher also can be referred to as a "quencher group".

"Quenching" as used herein refers to a process that reduces or changes at least one optical property of a semiconductor nanocrystal. Such optical properties include fluorescence emission intensity, emission wavelength, quantum yield, or radiative lifetime. Quenching of a semiconductor nanocrystal can produce a "quenched" semiconductor nanocrystal. Quenching can result from contact or interaction of a nanocrystal with a chemical group (or a plurality of groups), referred to herein as a "quencher group" or "quencher".

An "activator" as used herein refers to a compound, group, or energy field that can restore or enhance at least one optical property (e.g., fluorescence emission) of a semiconductor nanocrystal. An activator can be a chemical group (or a plurality of groups) or a redox carrier such as an electron or a hole, in which case the activator also can be referred to as an "activator group". Alternatively, light can serve as an activator.

"Activation" as used herein refers to a process that restores or enhances at least one optical property of a semiconductor nanocrystal (e.g., fluorescence emission intensity, quantum yield, and the like). Activation can result from contact or interaction between a semiconductor nanocrystal and an "activator". Activation of a semiconductor nanocrystal can produce an "activated" semiconductor nanocrystal. As with quenching, the interaction between the nanocrystal and the activator can be permanent or transient. Activation can be achieved using a chemical activator group or by irradiating the nanocrystal with light. Photoactivation can be achieved using a light source and can be used alone or in combination with a chemical activator group. Chemical activation and/or photoactivation can be performed on a nanocrystal prior to or after treatment with a quencher group and can enhance an optical property to varying degrees.

Disclosed herein are fluorogenic semiconductor nanocrystals and methods of their manufacture and use. Also provided are methods of restoring and enhancing one or more optical properties (e.g., emission intensity or quantum yield) of fluorogenic semiconductor nanocrystals and applications of such nanocrystals.

The semiconductor nanocrystals provided herein include a semiconductive, optically active core. The core can be surrounded by one or more semiconductor shell layers. The semiconductor shell can provide a physical barrier between the optically active core and the surrounding medium. The shell is substantially uniform in coverage around the core and is substantially free of defects. The shell can take a variety of forms. For example, the shell can be a multi-layer shell or an alloyed shell. In certain embodiments, the shell forms a substantially concentric overcoating about the core. In certain embodiments, the shell can include multiple layers that form an onion-like overcoating about the core. The presence of the external shell can reduce the nanocrystal's sensitivity to environmental changes, reduce photo-oxidation, and can help passivate surface trap states to significantly enhance fluorescence quantum yield.

The nanocrystal core and shell can be made of any suitable metal and non-metal atoms that are known to form semiconductor nanocrystals. Suitable semiconductor materials for the core and/or shell include, but are not limited to, ones including Group 2-16, 12-16, 13-15 and 14 element-based semiconductors such as ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlAs, AlP, AlSb, PbS, PbSe, Ge and Si and mixtures thereof. In some embodiments, the core and the shell of a core/shell nanocrystal are composed of different semiconductor materials, meaning that at least one atom type of a semiconductor material of the core of a core/shell is different from the atom types in the shell of the core/shell nanocrystal.

Suitable materials for the shell typically include a semiconductor material having a higher bandgap energy than that of the semiconductor nanocrystal core, however, other arrangements are also possible. In addition to having a bandgap energy greater than the semiconductor nanocrystal core, suitable materials for the shell can, in certain embodiments, have good conduction and valence band offset with respect to the core semiconductor nanocrystal. Thus, the conduction band is desirably higher and the valence band is desirably lower than those of the core semiconductor nanocrystal. The shell and core materials are typically chosen to minimize lattice mismatch. For semiconductor nanocrystal cores that emit energy in the visible (e.g., CdS, CdSe, CdTe, ZnS, ZnSe, ZnTe, GaP, GaAs, GaN) or near IR (e.g., InP, InAs, InSb, PbS, PbSe), a material that has a bandgap energy in the ultraviolet regions may be used. Exemplary materials include CdS, CdSe, InP, InAs, ZnS, ZnSe, ZnTe, GaP, GaN, and magnesium chalcogenides, e.g., MgS, MgSe, and MgTe. For a semiconductor nanocrystal core that emits in the near IR, materials having a bandgap energy in the visible, such as CdS or CdSe, may also be used. It is also understood in the art that the actual fluorescence wavelength for a particular nanocrystal core depends upon the size of the core as well as its composition, so the categorizations above are approximations, and nanocrystal cores described as emitting in the visible or the near IR can actually emit at longer or shorter wavelengths depending upon the size of the core.

In certain embodiments, the core and/or shell includes a mixture of at least one Group II element and at least one Group VI element (e.g., CdSe or CdTe or a mixture thereof) or a Group II-VI-VI, or a Group II-II-VI semiconductor material. In some embodiments, the semiconductor nanocrystal includes a CdSe core. In certain embodiments, a fluorogenic nanocrystal is provided that does not include CdTe. In other embodiments, the core includes a mixture of at least one Group III element and at least one Group V element (e.g., GaAs, InGaAs, InP, InAs, or InGaP or a mixture thereof). In certain embodiments, the semiconductor shell layer can include CdZnS, ZnS, CdS, CdSeS, ZnSeS, CdZnSeS, ZnSe, or a combination of these materials. In certain constructions, the shell layer can further include a rare earth metal, Cu, Mg, Ag, Hg, Pb, Mn, Ni, Co, Fe, Au, Be, Cr, P, B, N, O, Ge, Ga, or Si atoms.

Nanocrystals as disclosed herein can absorb a wide spectrum of wavelengths, and emit light in a relatively narrow range of wavelengths. The excitation and emission wavelengths are typically different, and non-overlapping. The color (i.e., emitted light) of a semiconductor nanocrystal can be "tuned" by varying the size and composition of the particle. Depending on the size of the nanocrystal core, these nanocrystal(s) can emit in the UV, visible or IR portions of the electromagnetic spectrum. The emission maxima of the disclosed nanocrystal or populations thereof can generally be at any wavelength from about 200 nm to about 2500 nm. In certain embodiments, nanocrystals are provided that emit in the UV or visible range of electromagnetic spectrum (below about 800 nm). In yet other embodiments, the population emits in the near-IR regions of the spectrum (e.g., between about 700 nm to about 2500 nm). Typically, nanocrystals are sized to provide fluorescence in the UV-IR portion of the electromagnetic spectrum, as this range is convenient for use in monitoring biological events in relevant media.

The disclosed nanocrystal(s) can have any diameter, where the diameter is measured along the shortest axis of the nanocrystal. Nanocrystals can range in diameter from about 1 to about 1000 nm. Typically, the nanocrystal has a diameter of about 1 nm to about 100 nm; or about 1 nm to about 20 nm; or about 1 nm to about 15 nm; or about 1 nm to about 10 nm or a diameter ranging between any two of these values.

In certain embodiments, the nanocrystal populations disclosed herein can include a plurality of individual nanocrystals that are of substantially identical size and shape. Such a collection of particles is sometimes referred to as being a "monodisperse" population. Monodisperse populations of nanocrystals can be prepared that are capable of emitting light of a single color (also referred to as a single color preparation). One of ordinary skill in the art will realize that particular sizes of nanocrystals can be obtained as particle size distributions. Thus, also provided herein are populations of nanocrystals where greater than 75% (e.g., greater than 80%; or greater than 85%; or greater than 90%; or greater than 95%) of the nanocrystals in the population have substantially identical diameters.

The nanocrystal populations described herein can be characterized in that they can produce a fluorescence emission having a relatively narrow wavelength band indicative of a population of similarly sized (i.e., monodisperse) nanocrystals. The width of ensemble emission band is typically less than about 60 nm full width at half maximum (FWHM), or less than about 50 nm FWHM, or less than about 40 nm FWHM, or less than about 30 nm FWHM or less than about 20 nm FWHM, when measured at room temperature. The emitted light preferably has a symmetrical (e.g., Gaussian), monomodal emission band. Certain materials provided herein exhibit astounding color purity (e.g., less than about 30 nm FWHM) indicative of a highly monodisperse population, as well as favorable optical properties (e.g., minimal intermittent blinking, high extinction coefficient, high quantum yield, photostability or a combination of two or more of these properties).

Certain nanocrystals provided herein can have high extinction coefficients and high quantum yield in the absence of the quencher group(s). The extinction coefficient can be measured at various wavelengths, although it is generally most practical to use an excitation wavelength of 405 nm (i.e., the wavelength used in many commercial lasers). At this excitation wavelength, the extinction coefficient for certain disclosed nanocrystals typically ranges from about 3,000,000 $cm^{-1}M^{-1}$ to about 30,000,000 $cm^{-1}M^{-1}$. For example, the nanocrystals described herein can exhibit an extinction coefficient measured at an excitation wavelength of 405 nm of about 3,000,000 $cm^{-1}M^{-1}$ to about 10,000,000 $cm^{-1}M^{-1}$; or about 10,000,000 $cm^{-1}M^{-1}$ to about 20,000,000 $cm^{-1}M^{-1}$; or about 20,000,000 $cm^{-1}M^{-1}$ to about 30,000,000 $cm^{-1}M$.

Certain nanocrystals disclosed herein also can exhibit a high quantum yield (i.e., ratio of photons emitted to photons absorbed) in the absence of the quencher group(s). Such nanocrystals can have a quantum yield (QY) of at least about 10%, at least about 20%, at least about 40%, at least about 50%, at least about 60%, at least about 70%, at least about 80%, at least about 90%, at least about 95%, at least about 98%. Quantum yield can be measured in either an aqueous or an organic medium. Certain nanocrystals (or a population thereof) provided herein exhibit a QY of about 60% or greater; or about 70% or greater; or about 80% or greater; or about 85% or greater when measured in either an aqueous or organic medium (e.g., solvent).

The nanocrystal(s) provided herein can further include a surface coating in direct contact with the external shell layer that can impart certain physical/chemical characteristics to the nanocrystal(s), protect the nanocrystal(s) from degradation, and/or allow the nanocrystal(s) to bind to biomolecules.

Typically, nanocrystals are prepared in hydrophobic, organic solvents that remain on the nanocrystal surface. Fluorogenic nanocrystals can prepared from such hydrophobic nanocrystals. However, in some embodiments, the disclosed nanocrystal(s) include a coating on the surface of the semiconductor nanocrystal adding various functionalities that render the nanocrystals water-dispersable or soluble in aqueous solutions. In certain embodiments, the nanocrystal includes a hydrophilic layer on the surface of the semiconductor nanocrystal that renders the nanocrystal water-dispersible.

There are a number of suitable coating materials that can be applied to nanocrystals to form a hydrophilic layer on the nanocrystal surface. Typically, these coating materials include a group(s) for attachment to the nanocrystal surface and a hydrophilic group(s), such as carboxylic acids, hydroxyls, amines, and the like. Attachment of the coating material to the nanocrystal surface can involve any form of covalent or non-covalent association. In certain embodiments, the coating materials can include small organic ligands, which include a hydrophilic component.

A number of suitable surface coatings can be employed to permit aqueous dispersibility of the described nanocrystals, including, but not limited to, lipids, phospholipids, fatty acids, polynucleic acids, polyethylene glycol (PEG), polyacrylic acids, polyacrylamides, RAFT polymers, thiol-containing polymers, imidazole-containing polymers, peptide-containing polymers, and polypeptides. In certain embodiments, the surface coating provides a hydrophilic layer formed of an amphiphilic polymer, such as an acrylic acid-based polymer.

Other coating materials include thiol containing compounds (e.g., mercapto carboxylic acids, such as mercaptoundecanoic acid, MUA), bidentate thiols (e.g., dihydrolipoic acid, DHLA), tridentate thiols, oligopeptides (e.g., dipeptides), amine or carboxylic acid containing organic molecules (e.g., hexadecylamine, HDA), functionalized organophosphorous compounds (e.g., phosphonic acids, phosphinic acids), hydrophilic phosphonic acids, or hydrophilic oligimers having phosphonate, phosphinate, amine, carboxylate, thiol, imidazole, phosphine, nitrile, or isonitrile functionality. In certain embodiments, an inorganic (non-semiconductor) shell layer, such as zirconia, titania, silica, ZnS, ZnO, or MgO, can be applied over the semiconductor shell layer to impart beneficial surface properties to the nanocrystal.

In another aspect, the nanocrystal can further include one or more biological molecules (i.e., biomolecules) linked to the surface coating of the semiconductor nanocrystal. In certain embodiments, a plurality of biological molecules is linked to the semiconductor nanocrystal. For certain applications, it may be desirable to link an additional organic molecule or biomolecule to the nanocrystal surface or to the hydrophilic layer. For example, the nanocrystal can include a surface coating capable of linking to a biological molecule or other type of organic molecule. Biological molecules include, for example, nucleic acid polymers, oligonucleotides, aptamers, nucleotides, proteins, antibodies, enzymes, peptides, carbohydrates, amino acids, polypeptides, protein, polysaccharides, lipids, biotin, streptavidin, and the like). Other organic molecules include, for example, dyes, quenchers (e.g. methylviologen), metal ligands (e.g. NTA) and the like.

In certain embodiments, the semiconductor nanocrystal is associated with a ligand or ligands that include an activator group or a plurality thereof, as disclosed herein. For example, a nanocrystal can include a multi-functional polymer coating on the surface of the nanocrystal, where the coating can include the activator (e.g., isonitrile group). An activator-containing coating can promote activation without the need to add the activator in a separate step.

In other embodiments, the nanocrystal is conjugated to a molecule that includes a histidine group. For example, nanocrystals coated with DHLA can be conjugated to a His6-modified protein (e.g, polymerase or glucosidase), with optional inclusion of coating proteins such as BSA or inert $His_6$-modified proteins.

In yet other embodiments, the nanocrystal includes a surface layer that includes one or more reactive groups, such as amino, azide, alkyne, cycloalkyne, phosphine, carboxylic acid, maleimido, thiol, and succinimidyl ester. In certain embodiments, the surface layer includes alkyne reactive groups (e.g., azido groups) or azide reactive groups (e.g., terminal alkynes). Such reactive groups can be conjugated to various types of molecules. For example, a nanocrystal can be provided with an azide reactive group or an alkyne reactive group for conjugation with a reaction partner in a 1,3-dipolar cycloaddition reaction (e.g., click reaction). Reactive groups on the nanocrystal surface can be linked to various types of materials to form conjugates, including, but not limited to, any of the biological and organic molecules described herein.

Examples of commercially available semiconductor nanocrystals that can be used in the compositions and the methods described herein include any of the QDOT nanocrystals (e.g., nanocrystals with fluorescence emission at 525, 545, 565, 585, 605, 625, 655, 705 or 800 nm) from Life Technologies Corporation (Carlsbad, Calif.), including, without limitation, QDOT nanocrystal conjugates (e.g., streptavidin conjugates) and functionalized nanocrystals. Other examples of suitable nanocrystals include those derivatized with carboxyl groups, amino (PEG) groups and aliphatic hydrocarbon groups (available under the tradename QDOT Innovator's Toolkit (ITK)), as well as reactive nanocrystals, such as provided in the QDOT Antibody Conjugation Kits, and QTRACKER Cell Labeling Kits and Non-Targeted Quantum Dots.

The fluorogenic semiconductor nanocrystal can include a fluorescent semiconductor nanocrystal and one or more quencher groups associated with the semiconductor nanocrystal. The fluorogenic semiconductor nanocrystal includes an optically active, semiconductor core and typically includes a semiconductor shell layer disposed on the semiconductor core material. In the absence of the quencher group, the semiconductor nanocrystal is optically active and capable of fluorescing upon excitation at an appropriate wavelength. Such fluorescent nanocrystals typically emit light in the visible or near IR spectral range. In association with a quencher group(s), the intensity fluorescence emission of the fluorescent semiconductor nanocrystal is reduced or even quenched entirely. If quenching is complete, a fluorogenic nanocrystal or population thereof emits no light or emits light at a level below the detection limit of the detector, the nanocrystal or population thereof is considered non-emissive.

The quencher can be any group or compound that is capable of reducing the nanocrystal's fluorescence emission intensity upon association with the semiconductor nanocrystal. The quencher group can associate with the nanocrystal in a permanent or reversible manner. In certain embodiments, the quencher group can be a metal source. Examples of metal sources include a metal atom or metal ion or can be a component of a metal-containing compound, such as an organometallic compound or a metal salt. The quencher group can be or include a transition or non-transition metal ion, such as Cu(I), Cu(II), Ag (I), Hg (I,II), Pb (II), Pb(IV), Fe (II), Fe(III), Co (II), Ni (II), and Cr (I, II, III, IV, V, or VI). In certain embodiments, the quencher group includes a copper source (e.g., a Cu(I) or Cu(II) ion). In certain embodiments, it may be desirable that the quencher group does not include a Cu (II) ion. In other embodiments, the quencher group is an anion, such as $F^-$, $Cl^-$, $S^{2-}$, $Se^{2-}$, $I^-$, $Br^-$, $O^{2-}$, oxyanions (e.g., sulfate, phosphate, borate, silicate, nitrate, and the like), reactive oxygen species (e.g., OH radical, peroxide, singlet oxygen, and the like), a reducing agent (e.g., ascorbate, cobaltacene, low valent metals such as Cu, Ag, Fe, and the like), or an oxidizing agent (e.g., $Br_2$, $I_2$, $Cl_2$, $F_2$, ferrocinium, nitosonium, nitric oxide, and the like).

The fluorogenic semiconductor nanocrystal provided herein can include at least one quencher group, but typically a plurality of quencher groups is associated with the nanocrystal. The number of quencher groups associated with the semiconductor nanocrystal can range from a single group to many thousands of such groups. The number of quencher groups is typically less than about 5000; or less than about 4000; or less than about 3000. For example, the number of quencher groups can range from about 1 to about 50; or about 50 to about 100; or about 100 to about 500; or about 500 to about 1000; or about 1000 to about 1500; or about 1500 to about 2000; or about 2000 to about 2500; or about 2500 to about 3000. In certain embodiments, the number of quencher groups associated with the nanocrystal is greater than 50 (e.g, 50 to about 3000).

The quencher group, upon association with a fluorescent nanocrystal, causes a reduction in the fluorescence emission intensity exhibited by the fluorescent nanocrystal prior to association with the quencher group. The emission intensity can be reduced to varying degrees. The amount of quenching achieved is described by comparing the initial fluorescence intensity of the fluorescent nanocrystal ($F_0$) prior to association with the quencher group(s) and the fluorescence intensity of the nanocrystal after association with the quencher group(s) ($F_Q$). This relationship, expressed as a ratio $F_Q/F_0$, is referred to herein as the "quenching ratio". The value of the quenching ratio depends on the composition of the fluorescent semiconductor nanocrystal, as well as the number and type of quencher groups associated with the nanocrystal. The quenching ratio can range from 0 to 1.0, where a ratio of 0 indicates that the nanocrystal exhibits no detectable emission (i.e., non-emissive). Nanocrystals which have a quenching ratio of greater than 0 but are not readily detectable using standard methods can be considered substantially non-emissive. The quenching ratio for a fluorogenic nanocrystal is typically less than 1.0; or less than 0.90; or less than 0.80; or less than 0.70; or less than 0.60; or less than 0.50; or less than 0.40; or less than 0.30; or less than 0.20; or less than 0.10. For many applications, the quenching ratio is typically less than 0.50.

Also provided herein are compositions and kits that include a fluorogenic nanocrystal or a population thereof, as described herein. In certain embodiments, the nanocrystals are formulated for use in an in vitro or in vivo biological assay. Such compositions can be aqueous or organic dispersions (e.g., colloidal dispersions) of nanocrystals. A population of fluorogenic nanocrystals can be dispersed in an aqueous medium (e.g., water or buffer) or an organic medium (e.g., an organic solvent or a polymer). This medium can be in the form of a liquid or a solid. In one embodiment, provided herein are stable (non-aggregated) dispersions of fluorogenic semiconductor nanocrystals in an aqueous medium. In certain embodiments, the fluorogenic semiconductor nanocrystal can be associated with a solid medium. In some embodiments, the nanocrystals are associated with a solid support, such as a glass, polymer, or metal. Suitable supports include, for example, a bead (e.g., polymer, magnetic, or glass bead), microsphere, slide, fiber, microchip, microfluidic channel, microwell plate, nanowell, magnetic disk, or a magnetic tape. Also provided herein are methods for applying such compositions to such supports. In certain embodiments, compositions can further include an activator, such as, for example, a cyanide source (e.g., a cyanide salt or an organocyanide compound), as discussed below.

Also disclosed herein are methods of making a fluorogenic semiconductor nanocrystal and populations thereof. In general, a fluorogenic nanocrystal can be prepared by associating a fluorescent semiconductor nanocrystal with one or more quencher groups to diminish the fluorescence emission intensity of the fluorescent nanocrystal. In a general method, a reaction mixture that includes at least one fluorescent semiconductor nanocrystal and at least one solvent is provided. Any fluorescent semiconductor nanocrystal described herein can be used in the described method. Likewise, any suitable solvent can be used to disperse the nanocrystals in the reaction mixture. One or more quencher groups then are added to the reaction mixture in an amount sufficient to reduce the fluorescence emission of the semiconductor nanocrystal. Any quencher group described herein can be used in the disclosed method. Typically, the solvent used in the reaction mixture is also capable of also dissolving or dispersing the quencher groups in the reaction mixture.

Typically, the amount of quencher groups added to the reaction mixture is sufficient to reduce the fluorescence emission signal of the nanocrystals by at least 50% upon addition of the quencher group. The concentration of quencher groups added to the reaction mixture depends on the desired number of quencher groups to be associated with each semiconductor nanocrystal. The concentration of quencher groups in the reaction mixture typically ranges from about $10^{-8}$ M to about $10^{-3}$ M. For example, quencher groups can be added to the reaction mixture in an amount such that greater than 50 quencher groups are associated with each nanocrystal (i.e., 50:1 quencher group to nanocrystal ratio). In certain preparations, the ratio of quencher groups per nanocrystal present in the reaction mixture is about 50 to about 3000; or about 50 to about 1000; or about 1000 to about 2000; or about 2000 to about 3000.

The quencher groups can be incubated in the presence of the fluorescent nanocrystals for a time sufficient to associate quencher groups with the semiconductor nanocrystal. Incubation can be conducted at room temperature or at elevated temperature. The temperature can be selected to optimize controlled deposition of quencher groups on the surface of the nanocrystal and to minimize aggregation of the nanocrystals and/or quencher groups.

The methods described herein can be conducted in a solvent or a solvent mixture. The type of solvent depends on the surface properties of the nanocrystal. Hydrophobic nanocrystals are readily dispersed in or dissolved in a water-immiscible solvent like hexanes, toluene, and the like, and are not readily dispersed in water. Alternatively, hydrophilic nanocrystals can be dispersed in an aqueous solvent (e.g., water or buffer).

Once the quenching groups and the semiconductor nanocrystals are combined, the reaction mixture is incubated. Typically, incubation is carried out at room temperature; however, elevated temperatures also can be used. The progress of the quenching reaction can be monitored spectroscopically. The reaction can be halted when nanocrystals achieve a certain minimum emission intensity (where the emission intensity is indicative of association of quencher groups with the nanocrystal surface). In certain embodiments, the reaction is halted once the nanocrystals no longer exhibit fluorescence emission. In certain embodiments, the reaction is halted when the emission reaches about 50%, or about 40%, or about 30%, or about 20%, or about 10% of the initial fluorescence intensity.

The methods disclosed herein can be applied to any type of hydrophobic or hydrophilic fluorescent semiconductor nanocrystal. When utilizing hydrophobic nanocrystals, the method can further include treating the semiconductor nanocrystal after addition of the quenching group with a hydrophilic compound that renders the nanocrystal water-dispersible. Further, an organic molecule, such as a biomolecule, which can optionally include one or more reactive groups, as disclosed herein, can be linked to the nanocrystal either prior to or after treatment of the nanocrystal with the quencher.

The novel materials provided herein offer unique spectral emission properties which allow these materials to be implemented in a variety of fluorescence based assays, such as immunosorbant assays (USA), enzyme-linked immunosorbant assays (ELISA), Western blot, ELISPOT, Fluorescent In-Situ Hybridization (FISH), gene detection, and PCR. Other applications include DNA sequence analyses; flow cytometry, fluorescence activated cell sorting assay; diagnostics in biological systems, in vivo and in vitro imaging (e.g., cellular imaging), single molecule microscopy and high throughput screening applications. Further, chemical switching methods are provided for achieving controlled manipulation of semiconductor nanocrystal optical properties. Chemical switching methods, as disclosed herein, facilitate the use of nanocrystals in a wide array of novel fluorogenic and digital microscopy assays.

The materials and methods provided herein also permit semiconductor nanocrystals to be used in conjunction with metal ions (e.g., copper catalysts) and metal substrates, which typically quench fluorescence of semiconductor nanocrystals. Thus, also provided are materials and methods for conducting metal-catalyzed conjugation on semiconductor nanocrystals.

One application of the fluorogenic nanocrystals provided herein is their use as fluorogenic probes for detection and quantification of biological and non-biological analytes (e.g., nucleic acids, antibodies, proteins, peptides, carbohydrates, and the like).

Thus, in one aspect, a method of detecting an analyte in a biological or non-biological sample is provided. In such methods, a sample is contacted with a fluorogenic semiconductor nanocrystal (or a population thereof) or a nanocrystal composition as described herein for a time sufficient for the nanocrystals to bind to the analyte in the sample, if present. The fluorescence emission of the semiconductor nanocrystal is then detected. Because the fluorescence emission of the fluorogenic nanocrystal has been quenched, such methods can utilize an activator to regenerate (i.e., reactivate) the fluorescence emission of the semiconductor nanocrystal.

Thus, also provided herein are methods of activating a fluorogenic semiconductor nanocrystal and populations of activated fluorogenic nanocrystals produced by such methods. In such activation methods, a fluorogenic semiconductor nanocrystal or a population thereof is contacted with one or more activators until an optical property (e.g., fluorescence intensity) of the fluorogenic semiconductor nanocrystal or population increases. The rate of activation and the endpoint fluorescence intensity in certain assays provided herein can be significantly enhanced with addition of an activator. Without wishing to be bound by theory, the quencher group may be desorbed from the nanocrystal surface upon contact with the activator, thereby restoring the fluorescence of the semiconductor nanocrystal. However, desorption of quencher groups is not a necessary requirement for activation to proceed.

In yet another aspect, methods are provided herein for enhancing the optical properties (e.g., quantum yield) of fluorescent semiconductor nanocrystals in the presence certain activators, even in the absence of quencher groups on the semiconductor nanocrystal.

Activation methods disclosed herein are typically performed at room temperature; however, activation temperatures can range from about 15° C. to about 60° C. Typically, activation is performed at a neutral or a slightly alkaline pH (e.g., pH greater than 7). Activation can be performed, for example, at a pH of about 8-10; or about 8; or about 9; or about 10.

The emission intensity of the fluorogenic nanocrystal can increase to varying degrees. The amount of activation achieved can be described by comparing the initial fluorescence intensity of the fluorogenic nanocrystal ($F_Q$), where the fluorogenic nanocrystal can be a quenched or non-quenched fluorescent nanocrystal, prior to contact with the activator (s) and the fluorescence intensity of the activated nanocrystal after association with the activator (s) ($F_A$). This relationship can be expressed as a ratio $F_A/F_Q$, and is referred to herein as the "fluorogenic ratio".

The fluorogenic ratio is generally greater than 1, where a ratio of 1 indicates no detectable change in the fluorescence emissions of the quenched and activated semiconductor nanocrystals. Fluorogenic nanocrystals having a fluorogenic ratio of about 1 are considered non-activated, whereas a fluorogenic nanocrystal with a fluorogenic ratio of greater than 1 is considered activated. The fluorogenic ratio for an activated nanocrystal can be greater than 1.0; or greater than 10; or greater than 100; or greater than 1000; or greater than 10,000, although higher ratios are also possible. For many applications, the fluorogenic ratio is greater than 10.

The value of the fluorogenic ratio depends on the composition of the fluorescent semiconductor nanocrystal, the number and type of quencher groups associated with the nanocrystal, and the number and type of activators used to activate the fluorescence emission of the quenched nanocrystal.

In one method, a fluorogenic nanocrystal is contacted with an activator or a plurality thereof, such that the intensity of the fluorescence emission of the population of nanocrystals increases by at least 10%; or at least 25%; or at least 50%.

In another method, a hydrophilic, fluorescent nanocrystal (e.g., a nanocrystal linked to multidentate thiol ligands) is contacted with an activator or a plurality thereof, such that the intensity of the fluorescence emission of the population of nanocrystals increases by at least 10%; or at least 25%; or at least 50%.

In addition to enhancement of fluorescence intensity, the quantum yield of the activated nanocrystals can remain high and is often equivalent to that of the nanocrystal prior to quenching. As such, the quantum yield of the population of activated semiconductor nanocrystals can be about 10% or greater; or about 25% or greater; or about 50% or greater; or about 75% or greater.

Various types of activators can be used in the compositions and methods provided herein, and the specific type of activator depends on the nature of the semiconductor nanocrystal and/or quencher group used in a particular nanocrystal preparation. The activator can be added directly (e.g., by adding a solution of an activator to a reaction mixture containing quenched nanocrystals). Alternatively, or in addition, a compound can be added in a dormant or protected state and then deprotected to release an activator in the presence of the nanocrystals. The activator typically is chosen to not emit detectable fluorescence in the same spectral range as the nanocrystal (e.g., in the visible and near IR region).

Examples of activators include reducing agents, oxidizing agents, metal ion scavengers, and metal chelating agents, although many other types of activators can be used in the compositions and methods provided herein. Activators also can be used in combination (e.g., as a mixture) to restore or enhance the optical properties of a semiconductor nanocrystal. Representative examples of activators include protons and various types of organic anions, such as cyanide, thiolate, carboxylate, halides (e.g. fluoride), pyrophosphate and hydroxide ions; and organic compounds, such as, for example, compounds that include a nitrile, isonitrile, azide, thiocyanate, amine, or imidazole group. Additional examples of activators include NO, CO, reactive oxygen species (ROS) and peroxide.

In certain embodiments, the activator is a cyanide source. A cyanide source can be any compound that contains or is capable of providing a cyanide group. A cyanide source can be a cyanide ion or a cyanide salt, such as, for example, NaCN, KCN, LiCN, or alkylammonium cyanides (e.g. tetrabutylammonium cyanide). In other embodiments, the cyanide source is an organocyanide compound. Examples of organocyanide compounds include p-toluenesulfonylmethyl isocyanide (TOSMIC), hydroxynitriles (e.g. mandelonitrile, acetone cyanohydrin, and the like) acylcyanides, and alkylcyanide esters. Alternatively, the cyanide source can be a compound that includes a group that can generate a cyanide ion under appropriate conditions. Such compounds include, e.g., isonitrile and nitrile-containing compounds, where isonitriles and nitriles can be hydrolyzed to release a cyanide ion.

The activator can be a metal ion scavenger that binds with or converts a metal ion to a stable complex. In the presence of the metal ion scavenger, trace amount of the metal ions can be sequestered or removed such that the fluorescence of the semiconductor nanocrystals can be preserved.

In other embodiments, the activator can be a metal chelating agent that can form a coordination complex with a metal ion. Metal chelating agents can include at least two organic acid groups such as carboxylic acid ($COO^-$) and phosphonic acid ($PO_3^{2-}$). The metal chelating agent can further include additional functional groups with lone pair electrons, such as amines (including primary, secondary or tertiary amines), hydroxy (—OH) or thiol (—SH) groups.

Examples of metal chelating agents include (ethylenedinitrilo)tetraacetic acid (EDTA), butylenediaminetetraacetic acid, (1,2-cyclohexylenedinitrilo)tetraacetic acid (CyDTA), diethylenetriaminepentaacetic acid, ethylenediaminetetrapropionic acid, (hydroxyethyl)ethylenediaminetriacetic acid (HEDTA), N,N,N',N'-ethylenediaminetetra(methylenephosphonic)acid (EDTMP), triethylenetetraminehexaacetic acid (TTHA), 1,3-diamino-2-hydroxypropane-N,N,N',N'-tetraacetic acid (DHPTA), methyliminodiacetic acid, propylenediaminetetraacetic acid, 1,5,9-triazacyclododecane-N,N', N"-tris(methylenephosphonic acid) (DOTRP), 1,4,7,10-tetraazacyclododecane-N,N',N",N'"-tetrakis(methylenephosphonic acid) (DOTP), nitrilotris(methylene)

triphosphonic acid, diethylenetriaminepenta(methylenephosphonic acid) (DETAP), aminotri(methylenephosphonic acid), 1-hydroxyethylene-1,1-diphosphonic acid, bis(hexamethylene)triamine phosphonic acid, 1,4,7-triazacyclononane-N,N',N''-tris(methylenephosphonic acid (NOTP), 2-phosphonobutane-1,2,4-tricarboxylic acid, nitrolotriacetic acid (NTA), citric acid, tartaric acid, gluconic acid, saccharic acid, glyceric acid, oxalic acid, phthalic acid, maleic acid, mandelic acid, malonic acid, lactic acid, salicylic acid, 5-sulfosalicylic acid, catechol, gallic acid, propyl gallate, pyrogallol, 8-hydroxyquinoline, cysteine, histidine, and polypeptides.

In certain embodiments, a metal chelating agent, such as EDTA is used in combination with an activator (e.g., a cyanide source). EDTA is a versatile chelating agent that can form 2-6 coordination bonds with a metal ion and can form a stable complex with various metal ions, such as $Cu^{2+}$, $Fe^{3+}$ and $Co^{2+}$.

The activator can be a polymer or a protein. Examples of polymers that can be used as activator include polyethyleneimine, polypeptides, polyacrylic acid (including chemically modified derivatives thereof), polymers made with RAFT polymerization and polyethylene glycol. In certain assays, it can be desirable to use an amine-containing polymer as the activator. Examples of proteins that can be used as activator include those derived from blood plasma, such as fetal bovine serum (FBS) and components thereof (e.g., bovine serum albumin (BSA), casein, goat serum, fish serum such as steelhead salmon serum (e.g., SEA BLOCK Blocking Buffer from Thermo Fischer Scientific Inc., Rockford, Ill.), antibodies, streptavidin, kinases, cytokines, intercellular proteins, membrane proteins, and extracellular proteins).

The activator can be contacted with the fluorogenic or fluorescent nanocrystal directly or can be generated in situ. In some embodiments, activation of a fluorogenic nanocrystal can be achieved in the presence of a cyanide source (e.g., cyanide ions). For example, cyanide ions can be delivered to the nanocrystal in the form of a cyanide salt such as KCN. Alternatively, cyanide ions can be generated in situ (e.g., by release of a cyanide source (e.g., an isonitrile or cyanide ion) from a cyanogenic substrate). In particular methods, cyanide ions are generated by hydrolysis of a nitrile and isonitrile-containing compound.

Cyanogenic substrates include organic compounds, such as isonitriles and nitriles, as described above, as well as cyanogenic enzyme substrates. Cyanogenic enzyme substrates include any compound that can function as a substrate for a catalyst such as an enzyme (e.g., a cyanogenic enzyme), where the enzyme is capable of cleaving the substrate to release a cyanide ion or a compound that includes a nitrile or an isonitrile group.

Suitable cyanogenic substrates include cyanogenic glucosides. Examples of cyanogenic substrates include glucosides (e.g. amygdalin, prunasin, dhurrin, vicianin, linamarin, lotaustralin), cyanohydrins, cyanohydrin esters, cyanohydrins inorganic phosphates, cyanohydrin amides, hydroxyl nitriles (e.g. acetone cyanohydrin, mandelonitrile, acyl cyanides, and cyanophosphoesters). The cyanogenic substrates provided herein can be used in conjunction with a cyanogenic enzyme. The cyanogenic enzyme is typically specific to a particular cyanogenic substrate. Exemplary cyanogenic enzymes include glycosidases, glucosidases (e.g., alpha and beta glucosidase), esterases, hydroxynitrile lyases, alkaline phosphotases, galactosidases, proteases, phophotases, and lactamases. Examples of beta-glucosidases include amygdalases (e.g., almond β-glucosidase) and linamarase. Examples of esterases include pig-liver esterase and pancreatic esterase.

In certain embodiments, the method further includes hydrolyzing the cyanogenic substrate after treatment with the cyanogenic enzyme. For example, certain cyanogenic enzyme substrates may release a cyanide source, such as an isonitrile group, and further hydrolysis may be needed to release a cyanide ion. Examples of compounds that can be used in this regard include lysase (e.g., α-hydroxynitrile lysase), esterase, protease, or galactase.

Activation of fluorogenic nanocrystals can serve as the basis for various types of fluorogenic assays. Used in this manner, the fluorogenic nanocrystals provided herein can serve as fluorogenic probes or reporters. The fluorogenic assays disclosed herein can be used to detect various types of analytes. For example, the analyte can be a biomolecule, such as a protein (including post-translationally modified proteins), peptide, nucleic acid, oligonucleotide, aptamer, lipoprotein, glycoprotein, carbohydrate, lipid, phospholipid, aminoglycan, enzyme, or antigen, a cell, or a small inorganic or organic molecule (e.g., drug, toxin, metal ion). Typically, such assays utilize one or more binding groups that are capable of binding to the analyte to be detected. Examples of binding groups include, without limitation, antibodies, oligonucleotides, aptamers, and other types of chemical binding groups (polymers, metal ligands, protein binding chemicals, activity probes).

An exemplary fluorogenic assay for detecting the presence of a target analyte in a sample is an enzyme-based, homogeneous proximity assay. Referring to FIG. 1, a sample 101 (e.g., a biological sample) is contacted with a fluorogenic semiconductor nanocrystal 102 that is associated with a first binding group 103 (e.g., an antibody) capable of binding to an analyte 104 (e.g., an antigen) in the sample (if present). The sample is further contacted with a second binding group 105 (e.g., a second antibody) that is different from the first binding group and also capable of binding to the same analyte 104. In certain assays, the second binding group is associated with a cyanogenic enzyme 106. A cyanogenic substrate (not shown) that is capable of releasing a cyanide source (e.g., cyanide ion or an isonitrile group) is then added to the sample. When in proximity to the cyanogenic enzyme 106, the cyanogenic enzyme releases the cyanide source from the cyanogenic substrate, thereby activating the fluorogenic nanocrystal. The fluorescence emission of the activated semiconductor nanocrystal 107 is detected during the course of the assay, where an increase in the intensity of fluorescence emission signal of the nanocrystal (typically at least 25%) indicates the presence of the analyte in the sample.

Figure 2:
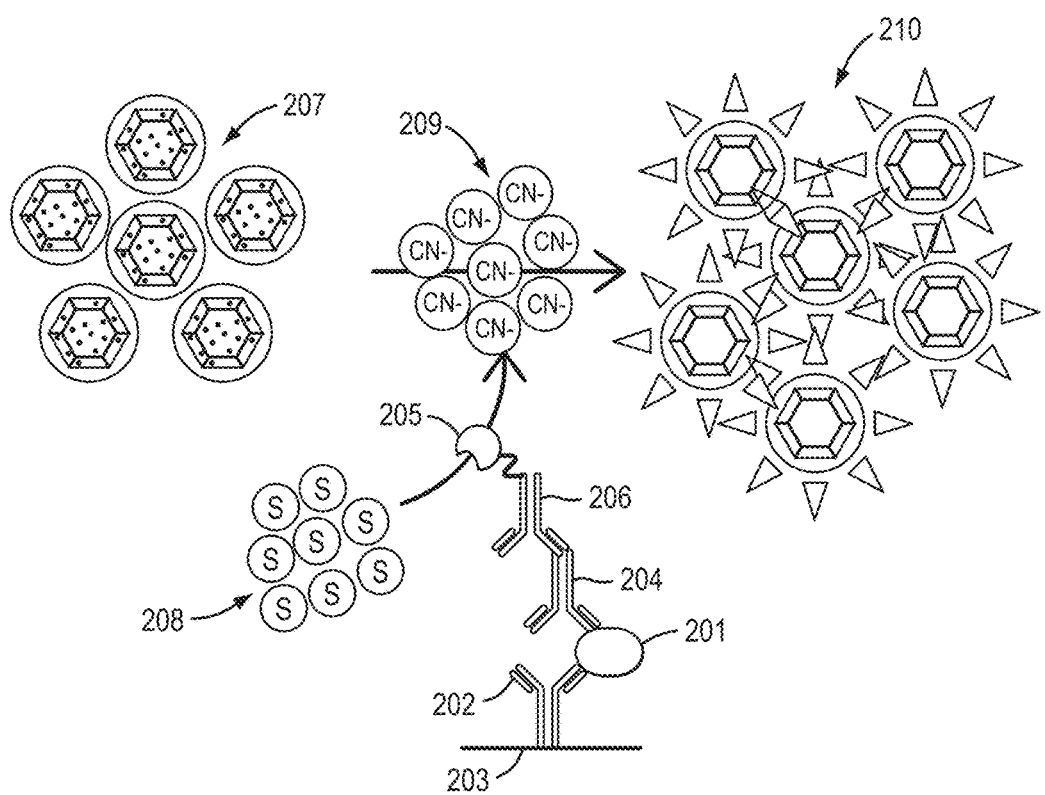
FIG. 2 illustrates an ELISA assay using a fluorogenic nanocrystal as disclosed herein.

The fluorogenic semiconductor nanocrystals disclosed herein also can be utilized in various types of ELISA assays. Referring to the exemplary assay depicted in FIG. 2, a sample containing an analyte 201 to be detected (e.g., an antigen) is contacted with two different types of binding groups (e.g., antibodies), both of which are capable of binding to the analyte. One of the binding groups 202 can be associated with a solid support 203 (e.g., a bead or plate). The second of the binding groups 204 is associated with a cyanogenic enzyme 205, either directly or indirectly through a third binding group 206 (e.g., antibody). A fluorogenic semiconductor nanocrystal 207 or a population thereof is added to the sample, and the sample is contacted with one or more cyanogenic substrates 208. A washing step can be performed to remove unbound species from the solid support prior to addition of the cyanogenic substrate. Once in proximity with the enzyme, the substrate releases a cyanide source 209 to activate the nanocrystals. Although the cyanide source is represented as a plurality of cyanide ions, any cyanide source can be utilized in the described assay. The fluorescence emission of the activated nanocrystals 210 is detected during the course of the assay, where an increase in the intensity of fluorescence emission signal (typically at least 25%) indicates the presence of the analyte in the sample.

Figure 3:
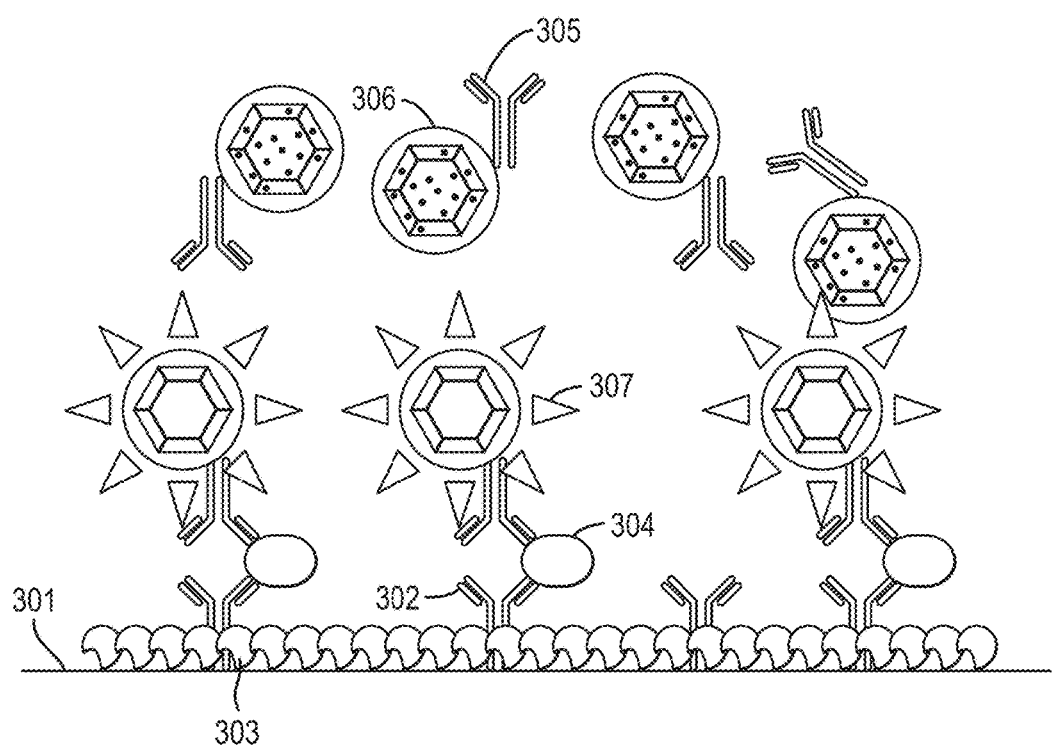
FIG. 3 illustrates a proximity ELISA assay using a fluorogenic nanocrystal as disclosed herein

The fluorogenic nanocrystals disclosed herein also can be implemented in a proximity ELISA assay. Referring to FIG. 3, a solid support 301 is provided that has bound to it a first binding group 302 (e.g., an antibody) and a cyanogenic enzyme 303. The first binding group and enzyme optionally can be connected. The solid support is contacted with a sample suspected of containing an analyte 304 and a different second binding group 305 (e.g., a second antibody), where both binding groups are capable of binding to an analyte in the sample, if present. The second of the binding groups 305 is associated with a fluorogenic nanocrystal 306, either directly (as shown in FIG. 3) or through a different, third binding group (e.g., antibody). This construct is then treated with a cyanogenic substrate (not shown). A further washing step can be performed to remove unbound species from the solid support prior to addition of the cyanogenic substrate. Upon contact with the cyanogenic enzyme, the substrate releases a cyanide source (not shown), thereby activating the fluorescence of the quenched nanocrystal to produce an activated nanocrystal 307. An increase in the intensity of fluorescence emission signal (typically at least 25%) indicates the presence of the analyte in the sample.

The fluorogenic semiconductor nanocrystals disclosed herein also can be used for detection of nucleic acids. One general method involves contacting a sample with a fluorogenic semiconductor nanocrystal that is associated with a first nucleic acid having a known sequence. The sample is then contacted with a second nucleic acid having a known sequence, wherein the second nucleic acid is associated with a cyanogenic enzyme. The sample then is contacted with a cyanogenic substrate. Upon contact with the cyanogenic enzyme, the cyanogenic substrate releases a cyanide source, thereby activating the fluorogenic nanocrystal. An increase in the intensity of fluorescence emission signal indicates the presence of a nucleic acid strand having a sequence capable of hybridizing to the first and second nucleic acid strands.

Also provided herein are fluorogenic assays systems. Exemplary systems can include a fluorogenic semiconductor nanocrystal or a population thereof, wherein the nanocrystal is associated with a first binding group. The system further includes a cyanogenic enzyme associated with a second binding group different from the first binding group. Both the first and the second binding groups are associated with or are capable of being associated with an analyte. The assay system can further include a cyanogenic substrate. The cyanogenic substrate can be capable of releasing a cyanide source (e.g., cyanide ion or an isonitrile group) upon contact with a cyanogenic enzyme. In certain embodiments, the cyanogenic enzyme and/or the second binding groups is associated with a solid support (e.g., bead or a microwell). Any of the binding groups, analytes, cyanide sources, substrates and enzymes provided herein can be in conjunction with the fluorogenic assay system.

In addition to the uses already mentioned, many other applications for the disclosed fluorogenic nanocrystals exist. One such application is a method is for identifying a cell or cellular component in a sample. In certain methods, individual populations of cells in a mixture of different types of cells can be encoded with fluorogenic nanocrystals. The method further includes exposing the sample to an appropriate excitation energy source to activate the semiconductor nanocrystals associated with the cell or cellular component. Detection of the fluorescence emission from the activated nanocrystal can be used to identify and/or track the cell or cellular component in the sample. In certain methods, the rate of activation and end point fluorescence can be further enhanced by use of a chemical activator as described herein. For example, the sample can be contacted with a polymer or protein (e.g., BSA, FBS or PEI) during the detection step to further accelerate and enhance activation.

In a representative method, a sample containing at least one cell is contacted with a fluorogenic semiconductor nanocrystal under conditions in which the nanocrystal is associated with the cell. The nanocrystal can be associated with the cell by being contained in the nucleus, in the cytoplasm, or in an organelle contained within the cell; embedded either in whole or in part in the cytoplasmic membrane, the nuclear membrane or any other membrane within the cell; is bound to a molecule within the cell or in the cell membrane; or otherwise fixed to the cell in a manner resistant to the environment or changes in the environment.

In the cell identification methods provided herein, the cell can be a member of a population of cells, where the population can include one or more types of cells. The cell(s) can be living or dead; and the cell(s) can be of any origin, including from prokaryotes, eukaryotes, or archeons. The cell(s) can be a cultured cell line or a primary isolate, the cell(s) may be mammalian, amphibian, reptilian, plant, yeast, bacterium, spirochetes, or protozoan. The cell(s) can be, for example, without limitation, a human, murine, rat, hamster, chicken, quail, goat or dog cell. The cell can be a normal cell, a mutated cell, a genetically manipulated cell, a tumor cell.

In certain methods, the method can be used for identifying a population of cells derived from an initial sample of one or more live cells via its unique spectral signature after several cell divisions. The ability to detect populations of cells derived from a few precursors by virtue of their spectral signature greatly facilitates the high-throughput analysis of many systems.

Also provided herein are fluorogenic assay systems for identifying a cell or cellular component in a sample. Exemplary systems can include a fluorogenic semiconductor nanocrystal or a population thereof, wherein each nanocrystal is associated with a cell or cellular component. Depending on the type of fluorogenic nanocrystal used in the assay, the system can further include a chemical activator as disclosed herein (e.g., a cyanide source and/or a polymer or protein such as BSA, FBS or PEI, to further accelerate and enhance activation of the fluorogenic nanocrystal.

The disclosed fluorogenic nanocrystals also can serve as sensitive cyanide sensors. Thus, also provided is a method of detecting cyanide ions in a sample (e.g., water or a biological sample such as blood, tissue, and the like). The sample suspected of containing cyanide ions is contacted with a fluorogenic semiconductor nanocrystal or population thereof, where the fluorogenic nanocrystal includes one or more quencher groups capable of complexing with a cyanide ion (e.g., Cu(I) or Cu(II) ion). The fluorescence emission is detected during the course of the assay. An increase in the intensity of fluorescence emission signal indicates the presence of the cyanide ions in the sample.

Thus, also provided herein are fluorogenic assay systems for detection of cyanide ions in a sample. Exemplary systems can include a fluorogenic semiconductor nanocrystal or a population thereof, wherein each nanocrystal includes one or more quencher groups capable of complexing with a cyanide ion (e.g., Cu(I) or Cu(II) ion).

The fluorogenic nanocrystals disclosed herein also can be used in a wide variety of digital detection and quantification techniques. In these methods, the fluorescence of fluorogenic nanocrystals can be chemically switched "on" or "off" in the presence of an activator or quencher group. In other methods, fluorogenic nanocrystals are switched "on" or "off" using pulses of light. In yet other methods, fluorogenic nanocrystals are switched "on" or "off" by application of an electrical potential to the nanocrystals.

Detection of the fluorescence emission of the nanocrystal can be indicative of the presence and location of the nanocrystal, as well as the number of fluorescent species in a sample. In one general method, a fluorescent semiconductor nanocrystal or population thereof or a fluorogenic nanocrystal or population thereof is contacted with a compound that serves to modulate the at least one optical property of the nanocrystal (e.g., fluorescence emission). Once activated, the position of the nanocrystal can then be determined by detection of the fluorescence emission generated by the nanocrystal.

Optical, chemical and electrical switching methods provided herein can be used in combination with various microscopy techniques to facilitate detection of nanocrystals. In certain embodiments, nanocrystals can be detected using the disclosed switching methods at the single-molecule level. Precise switching of the optical properties of the nanocrystals provided herein can alter the fluorescence emission and other optical properties of a single nanocrystal in a specific region of interest in a digital fashion. Used in this way, the fluorogenic nanocrystals provided herein can be implemented in many types of fluorescence-based, digital biology assays, including digital proteomics (e.g., proximity immunoassays), genomics and small-molecule detection.

In one embodiment, chemical switching can be achieved by contacting a fluorescent or fluorogenic nanocrystal with a quencher or activator(s), as disclosed herein, such that the intensity of the fluorescence emission of the nanocrystal decreases or increases. In embodiments that utilize a fluorogenic nanocrystal, the quenched, fluorescent nanocrystal can then treated with an activator(s) to rejuvenate the fluorescence of the nanocrystal, such that the intensity of the fluorescence emission of the nanocrystal increases. In certain assays, the nanocrystal is contacted alternately with activator and quencher groups to toggle emission "on" and "off" in a digital fashion. For certain assays, the nanocrystal or population thereof can be bound to a solid support (e.g., a glass slide) to facilitate repeated treatment with solutions of activator and quenchers or other wash solutions. The activated or quenched nanocrystal can then be detected spectroscopically to determine its presence (or absence) and/or location. In certain embodiments, in the presence of the quencher, the fluorescence emission of the nanocrystal is reduced by at least about 50%. Likewise, in the presence of the activator, the fluorescence emission of the quenched nanocrystal can increase by at least about 50%, and often is restored to its original (i.e., unquenched) value.

The rate and extent of activation of quenched and non-quenched nanocrystals with a chemical activator can be further enhanced and accelerated upon exposure to irradiation with light. In certain embodiments, light alone can be sufficient to cause appreciable activation of the nanocrystals, even in the absence of a chemical activator.

In certain methods, significant optical activation is achieved without the use of a chemical activator. For example, illumination of quenched fluorescent nanocrystals at an appropriate wavelength can activate the fluorescence of the nanocrystals, such that the intensity of the fluorescence emission of the nanocrystal increases. In certain assays, the nanocrystal is illuminated using pulses of light that serve to toggle emission "on" and "off" in a digital fashion. In certain assays, photoactivation can be toggled "on" and "off" to track fluorogenic nanocrystals in cells or cellular components.

Fluorogenic nanocrystals provided herein can activated optically. Optical activating can be achieved using any appropriate illumination source, e.g., laser, lamp, light-emitting diode, or the like. In certain embodiments, an evanescent field can be used to photoactivate fluorogenic nanocrystals that are bound to a surface. In other embodiments, a photonic bandgap structure is used to photoactivate a fluorogenic nanocrystal. Detection of the emitted light can be achieved with any suitable optical detection system that provides spectral information for the nanocrystal, e.g., grating spectrometer, prism spectrometer, imaging spectrometer, camera, or the like, or use of interference (bandpass) filters. Using a two-dimensional area imager such as a CCD camera, many objects can be imaged simultaneously. Spectral information can be generated by collecting more than one image via different bandpass, longpass, or shortpass filters (e.g., interference filters, colored glass filters, or electronically tunable filters). Once the data has been gathered, it can be processed to generate spectral information about objects in the image, or for each pixel, or group of pixels in the image, via standard image processing techniques.

Examples of imaging instruments and techniques that can be used to activate and/or image the fluorescent and fluorogenic nanocrystals disclosed herein, include, for example, fluorescence microscopy, total internal reflectance fluorescence (TIRF) microscopy, wide-field fluorescence microscopy, confocal fluorescence microscopy, fluorescence microplate readers, high-content imaging systems, fluorescence correlation spectroscopy (FCS), flow cytometers, including bead-based and acoustic focusing flow cytometers, such as the ATTUNE Acoustic Focusing Flow Cytometer (available from Life Technologies Corporation), fiber optics, waveguides, optical disks, microfluidics, and photonic bandgap structures (e.g., photonic crystals).

In certain methods, a photonic crystal having a periodic grating structure is used to activate and/or detect the presence of a fluorogenic nanocrystal in a sample. The sample and/or fluorogenic nanocrystal can be in close proximity to a photonic crystal surface. Typically, the fluorogenic nanocrystal is in contact with the crystal surface. Illumination of the photonic crystal at an appropriate wavelength and angle of incidence can induce an excitation resonance mode having a spectrum that overlaps the excitation spectrum of the fluorogenic nanocrystal and an extraction resonance mode having a spectrum that overlaps the emission spectrum of the nanocrystal. The excitation and extraction resonance modes resulting from illumination activates the fluorogenic nanocrystal and causes the nanocrystal to emit light. When used with the fluorogenic nanocrystals provided herein, photonic crystals can be used to significantly enhance the intensity and/or resolution of resulting nanocrystal image.

The nanocrystals provided herein also can be used in conjunction with super resolution microscopy (SRM) techniques to image fluorescent species at resolutions higher than the diffraction barrier. For example, SRM methods can be desirable to precisely determine the position of two different nanocrystals in close proximity to an accuracy that is less than the wavelength of the light emitted by first and/or second nanocrystal. A variety of high and super resolution microscopic (SRM) techniques are available and can be used to image the nanocrystals provided herein, including for example, structured illumination microscopy (SIM), stimulated emission depletion (STED), stochastic optical reconstruction microscopy (STORM), photoactivation localization microscopy (PALM), and bleaching/blinking assisted localization microscopy (BALM).

The discovery that certain activators provided herein can effectively rejuvenate the quenched fluorescence emission of metal-quenched semiconductor nanocrystals now provides the ability to implement semiconductor nanocrystals in a variety of new areas requiring contact with metallic and organometallic compounds, substrates (e.g., copper, brass, stainless steel, bronze, and the like), and metal catalysts (e.g., Cu(I) and Cu(II)).

An area of particular interest is the use copper-catalyzed, cycloaddition reactions, such as "click chemistry", for functionalization of semiconductor nanocrystals. "Click chemistry" typically refers to a 1,3-dipolar cycloaddition reaction between azides and alkynes. The reaction is performed in the presence of a copper catalyst (typically, copper ions).

Click chemistry is a powerful and widely used conjugation technique, especially for conjugation in aqueous media. However, functionalization of semiconductor nanocrystals using copper-catalyzed click reactions has not been practical to date, because the presence of the copper catalyst results in irreversible quenching of nanocrystal fluorescence emission. The use of certain activators provided herein (e.g., cyanide ions) now make it feasible to implement copper-catalyzed conjugation reactions for grafting molecules to a semiconductor nanocrystal surface.

Methods are provided herein for utilizing copper-catalyzed, click chemistry in conjunction with semiconductor nanocrystals. In a representative method for attaching a compound to a semiconductor nanocrystal using click chemistry, a fluorescent semiconductor nanocrystal that includes an alkyne reactive group or an azide reactive group is contacted with a reactive material that includes a group capable of reacting with the alkyne reactive group or azide reactive group in the presence of a copper catalyst (e.g., Cu(I) or Cu(II) ions). The nanocrystal conjugate can be contacted with an activator, as disclosed herein, such that the fluorescence emission intensity of the nanocrystal increases.

Examples of reactive materials include amino acids, peptides, proteins (including enzymes (e.g. polymerases), antibodies, avidin, and strepatavidin), carbohydrates, polysaccharides, nucleosides, nucleotides, oligonucleotides, nucleic acid polymers, drugs, lipids, synthetic polymers, biotin, and solid supports.

The reactive material can further include a label for detection (e.g., a dye). In certain embodiments of the methods for labeling modified semiconductor nanocrystals utilizing "click" chemistry described herein, the modified nanocrystal can possess an azide group, whereupon the label possesses an alkyne group. In other embodiments, the modified nanocrystal can possess an alkyne group, and the label possesses an azide group.

In certain embodiments, the alkyne or azide derivatized nanocrystal is water-dispersible, such that the reaction can be conducted in an aqueous medium. The copper source is typically added in the form of a solution. However, in certain embodiments, a fluorogenic nanocrystal quenched with copper ions is used. In such methods, the surface-bound copper ions can facilitate catalysis of the click reaction, such that the amount of additional copper ions can be reduced; and in some methods, additional copper ions may not need to be added at all. Thus, optionally, the click reaction can be conducted in the presence of at least one reducing agent.

In certain embodiments of the methods for labeling modified biomolecules utilizing "click" chemistry described herein, the solution comprising the "click" chemistry reactants will further comprise Cu(I) ions; Cu(I) ions and a copper chelator; Cu(II) ions and at least one reducing agent; or Cu(II) ions, at least one reducing agent, and a copper chelator.

Upon conjugation, it is typical that the fluorescence emission of nanocrystal conjugate diminishes or is even quenched entirely. Contact of the nanocrystal with an activator (e.g., a solution containing activators) causes the fluorescence emission intensity of the nanocrystal to increase. Representative activators that can be used to rejuvenate the nanocrystal emission after click conjugation includes a cyanide source as disclosed herein. In certain embodiments, the cyanide source includes cyanide ions, organocyanide compounds (e.g., isonitriles) or cyanogenic substrates, as disclosed herein. Treatment of conjugated nanocrystals with activators can restore the fluorescence emission of the nanocrystal to at least 50%; or at least 60%; or at least 70%; or at least 80%; or at least 90% of its initial value.

The copper used as a catalyst for the "click" chemistry reaction typically is in the Cu (I) reduction state. Suitable Cu(I) sources for use in copper-catalyzed azide-alkyne cycloadditions can be any cuprous salt including, but not limited to, cuprous halides such as cuprous bromide or cuprous iodide. The regioselective cycloaddition also can be conducted in the presence of a metal catalyst and a reducing agent. In certain embodiments, copper can be provided in the Cu (II) reduction state (for example, as a salt, such as but not limited to $Cu(NO_3)_2$ $Cu(OAc)_2$ or $CuSO_4$), in the presence of a reducing agent wherein Cu(I) is formed in situ by the reduction of Cu(II). Such reducing agents include, but are not limited to, ascorbate, tris(2-carboxyethyl) phosphine (TCEP), NADH, NADPH, thiosulfate, metallic copper, hydroquinone, vitamin $K_1$, glutathione, cysteine, 2-mercaptoethanol, dithiothreitol, $Fe^{2+}$, $Co^{2+}$, or an applied electric potential. In other embodiments, the reducing agents include metals selected from Al, Be, Co, Cr, Fe, Mg, Mn, Ni, Zn, Au, Ag, Hg, Cd, Zr, Ru, Fe, Co, Pt, Pd, Ni, Rh, and W.

Copper(I)-catalyzed azide-alkyne cycloadditions can be performed in water and a variety of solvents, including mixtures of water and a variety of (partially) miscible organic solvents including alcohols, dimethyl sulfoxide (DMSO), dimethyl formamide (DMF), tert-butanol (tBuOH) and acetone.

Copper ions can be unstable in aqueous solvents. Therefore, stabilizing ligands/chelators can be used to improve the efficiency of the reaction. In certain embodiments at least one copper chelator is used in the methods described herein, wherein such chelators binds copper in the Cu (I) state. In other embodiments, at least one copper chelator is used in the methods described herein, wherein such chelators binds copper in the Cu (II) state. In certain embodiments, the copper (I) chelator is a 1,10 phenanthroline-containing copper (I) chelator. Non-limiting examples of such phenanthroline-containing copper (I) chelators include, but are not limited to, bathophenanthroline disulfonic acid (4,7-diphenyl-1,10-phenanthroline disulfonic acid) and bathocuproine disulfonic acid (BCS; 2,9-dimethyl-4,7-diphenyl-1,10-phenanthroline disulfonate). In other embodiments, the copper(I) chelator is THPTA, N-(2-acetamido)iminodiacetic acid (ADA), pyridine-2,6-dicarboxylic acid (PDA), S-carboxymethyl-L-cysteine (SCMC), trientine, tetra-ethylenepolyamine (TEPA), N,N,N',N'-tetrakis(2-pyridylmethyl)ethylenediamine (TPEN), EDTA, neocuproine, N-(2-acetamido)iminodiacetic acid (ADA), pyridine-2,6-dicarboxylic acid (PDA), S-carboxymethyl-L-cysteine (SCMC), tris-(benzyl-triazolylmethyl)amine (TBTA), or derivatives thereof. In certain embodiments, EDTA is used as a chelator. In certain embodiments, histidine is used as a chelator, while in other embodiments glutathione is used as a chelator and a reducing agent.

The concentration of the reducing agents used in the "click" chemistry reaction described herein can be in the micromolar to millimolar range. In certain embodiments, the concentration of the reducing agent is from about 100 micromolar to about 100 millimolar. In other embodiments, the concentration of the reducing agent is from about 10 micromolar to about 10 millimolar. In other embodiments, the concentration of the reducing agent is from about 1 micromolar to about 1 millimolar.

The semiconductor nanocrystals provided herein also can be used in many other types of conjugation reactions, including, but not limited to cycloaddition reactions for the purpose of grafting molecules to the surface of the nanocrystal. For example, nanocrystals can be provided with azide and alkyne groups such that they can undergo catalyst free [3+2]cycloaddition by a using the reaction of activated alkynes with azides. Alkynes can be activated by ring strain such as, by way of example only, eight membered ring structures, appending electron-withdrawing groups to such alkyne rings, or alkynes can be activated by the addition of a Lewis acid such as, by way of example only, Au(I) or Au(III).

In certain embodiments of the methods for labeling modified nanocrystals utilizing activated alkynes described herein, the semiconductor nanocrystal can possess an azide group, whereupon the reaction partner possesses an activated alkyne group; while in other embodiments the modified nanocrystal can possess an activated alkyne group, and the reaction partner possesses an azide group.

Alternatively, conjugation of a molecule to the semiconductor nanocrystals provided herein also can be achieved using a Staudinger ligation reaction, which involves reaction between trivalent phosphorous compounds and organic azides, either of which can be associated with the semiconductor nanocrystal. The phosphines used in the Staudinger ligation methods described herein include, but are not limited to, cyclic or acyclic, halogenated, bisphosphorus, or even polymeric. Similarly, the azides can be alkyl, aryl, acyl or phosphoryl.

In certain embodiments of the methods for labeling modified nanocrystals utilizing Staudinger ligation described herein, the modified nanocrystal can possess an azide group, whereupon the reaction partner possesses a phosphine group, including, but not limited to, a triarylphosphine group; while in other embodiments the modified reaction partner can possess the phosphine group, and the label possesses an azide group.

The fluorogenic nanocrystals and compositions described herein also can form part of a kit. Kits for various biological applications and assays are provided herein.

Kit reagents for any of the kits disclosed herein can be packaged in the form of solutions can be packaged as a suspension in a liquid medium (e.g., water or an organic solvent) or be associated with a solid support (e.g., slide, microchip, bead, fiber, microwell plate, nanowell, magnetic disk, or magnetic tape). Kits disclosed herein also can be provided with instructions for using the kit.

In one embodiment, a kit comprises a population of fluorogenic nanocrystals for encoding a cell or cellular component. Additional buffers or other reagents useful for encoding a cell using the nanocrystal population also can be included in the kit (e.g., washing buffer, such as PBS, incubation buffer, and activators, including protein or polymers for enhancing activation). Additionally, the kit can be designed for multiplex applications and contain a plurality of fluorogenic nanocrystal populations useful for simultaneously encoding a plurality of different cell populations.

Kits disclosed herein can include an activator. For example, the activator can be a cyanide source such as a cyanide salt, an organocyanide compound, or a cyanogenic enzyme substrate, as well as a cyanogenic enzyme specific to the cyanogenic substrate and capable of cleaving the cyanogenic substrate to release cyanide ion or an isonitrile group.

Thus, in one aspect is provided a kit for conducting a fluorogenic essay that includes one or more populations of fluorogenic nanocrystals, as disclosed herein, and an activator(s), wherein the activator activates and enhances the fluorescence emission of the fluorogenic nanocrystal. For certain types of kits, the fluorogenic nanocrystals can be associated with one or more antibodies or oligonucleotides.

Kits are also provided for conducting cycloaddition reactions, e.g., click reactions. Kits for conducting copper-catalyzed cycloaddition reactions can include one or more populations of fluorescent semiconductor nanocrystals functionalized with an alkyne reactive group (e.g., azido group) or an azide reactive group (e.g., terminal alkyne, cyclooctyne, or phosphine); and can include a copper source, such as Cu(I) or Cu(II) ions; at least one activator, such as a cyanide source (e.g., cyanide salt or an organocyanide compound); and, optionally, at least one reducing agent.

In another type of kit for conducting cycloaddition reactions, the kit includes at least one population of fluorogenic semiconductor nanocrystals quenched with Cu(I) or Cu(II) ions and functionalized with alkyne reactive or azide reactive groups. In certain kits containing fluorogenic, copper-quenched nanocrystals, an additional copper source is not included.

The following examples are offered to illustrate but not to limit the embodiments described herein.

EXAMPLES

Example 1

Preparation of Quenched Semiconductor Nanocrystals in Aqueous Solvent

Figure 4:
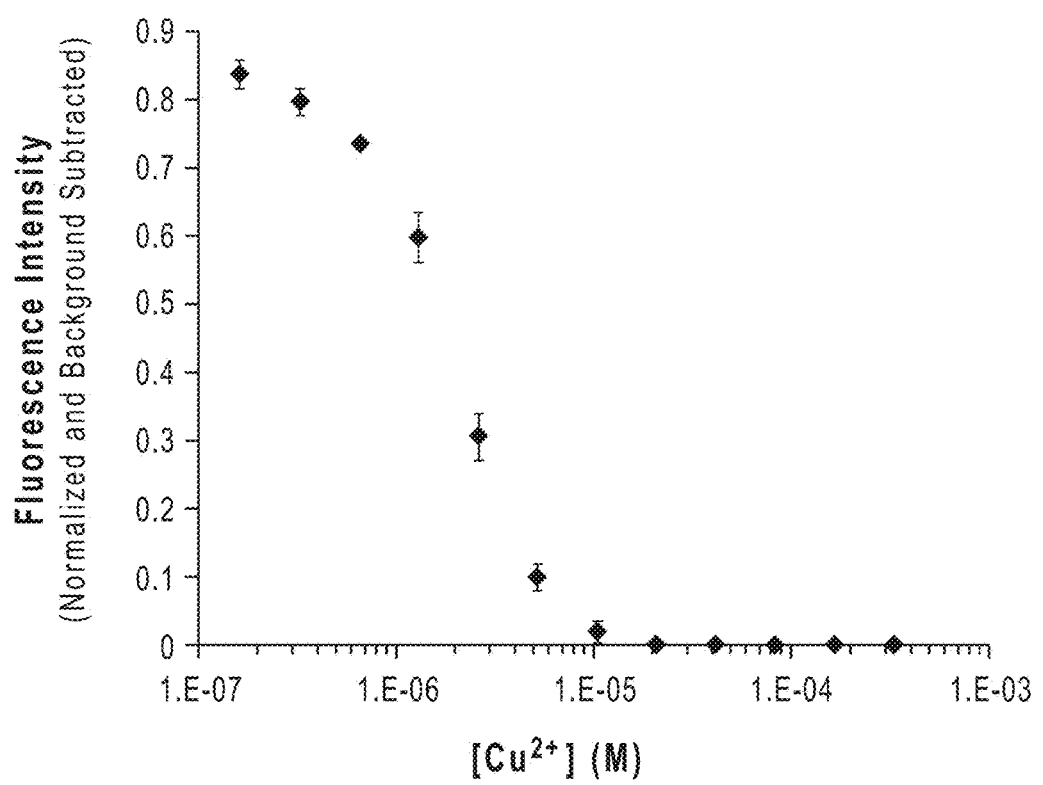
FIG. 4 is a plot showing the effect of copper ions on nanocrystal fluorescence emission.

The effect of copper ion concentration on fluorescence emission of hydrophilic semiconductor nanocrystals was determined as follows: A solution (100 nM-10 mM) of copper (II) sulfate in water or buffer was slowly added to an aqueous solution (1 nM-500 nM) of hydrophilic, semiconductor nanocrystals (e.g., QDOT carboxyl or amino semiconductor nanocrystals or QDOT streptavidin conjugates from Life Technologies Corporation, Carlsbad, Calif.). The combined solution was concentrated using ultra-filtration or purified using size-exclusion or ion-exchange chromatography. As shown in FIG. 4, fluorescence intensity of hydrophilic nanocrystals decreased as the copper ion concentration increased.

Example 2

Preparation of Quenched Semiconductor Nanocrystals in Non-Aqueous Solvent

Figure 5:
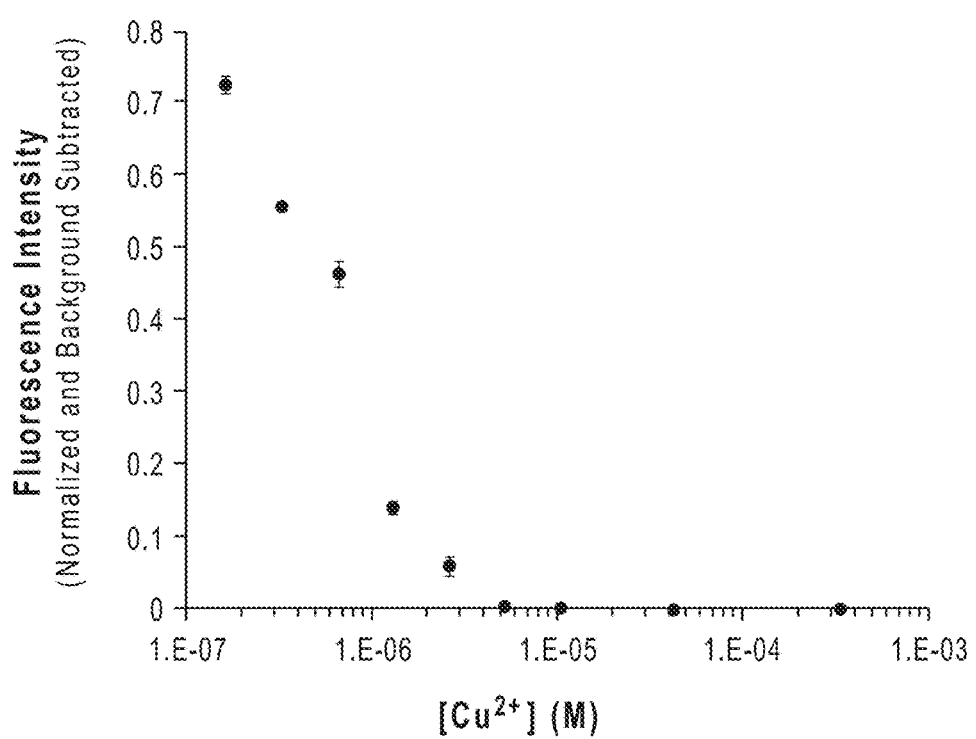
FIG. 5 is a plot showing the effect of copper triflate on nanocrystal fluorescence emission.

A solution (100 nM-10 mM) of a metal compound (e.g. copper (II) triflate) in an organic solvent (e.g. THF) was slowly added to a solution (10 nM-10 uM) of hydrophobic core/shell semiconductor nanocrystals in an organic solvent (e.g. chloroform). Hydrophobic, copper quenched particles can be further treated to make them water-dispersible. For example, particles can be precipitated using alcohols, collected by centrifugation, and then re-dispersed into a desired solvent. Alternatively, the hydrophobic particles can be exchanged into buffer using an amphiphilic polymer. FIG. 5 is a plot of fluorescence intensity for polymer coated nanocrystals as a function of copper ion concentration in the quenching solution.

Example 3

Cyanide Activation of Quenched Semiconductor Nanocrystals

Figure 6:
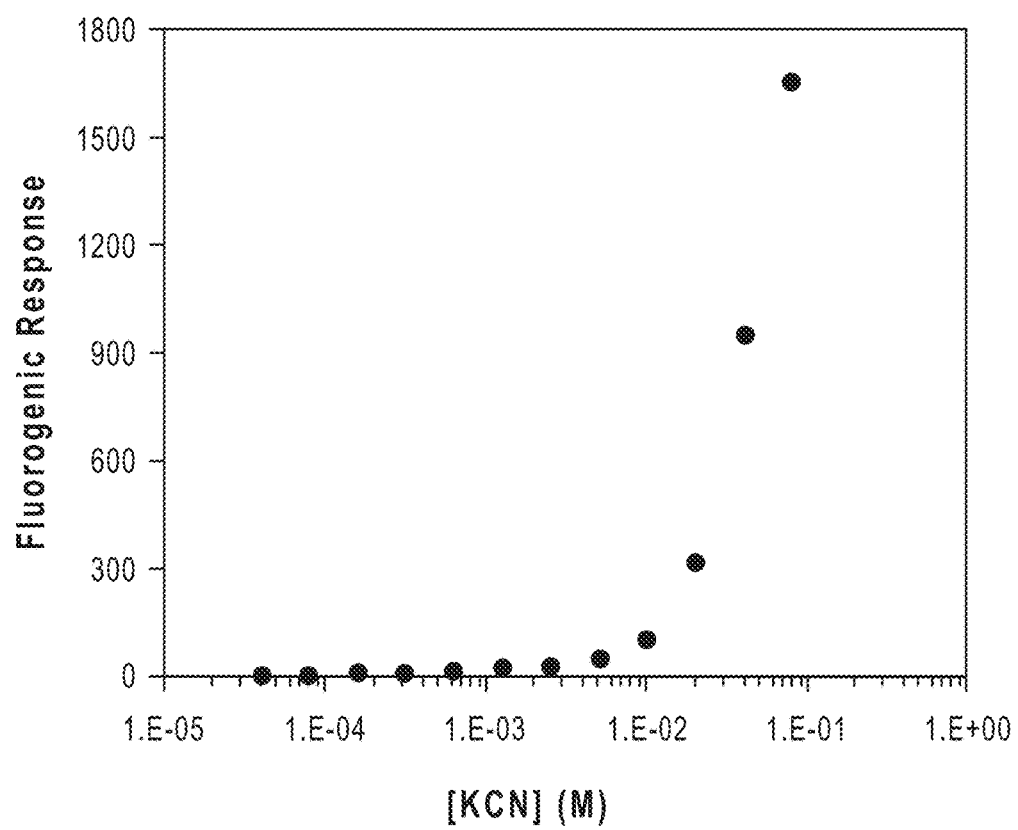
FIG. 6 is a plot showing the effect of cyanide ions on nanocrystal fluorescence emission.

A solution (10 uM-500 mM) of a cyanide salt (e.g. potassium cyanide) in water or buffer was added to a solution (1 nM-100 nM) of copper-quenched, semiconductor nanocrystals (QDOT 625 ITK carboxyl nanocrystals from Life Technologies Corporation) in water or buffer, prepared as described in Example 1 or Example 2. The fluorogenic response of the copper-quenched nanocrystals as a function of KCN concentration is shown in FIG. 6.

Example 4

Photoactivation of Quenched Semiconductor Nanocrystals

Figure 7:
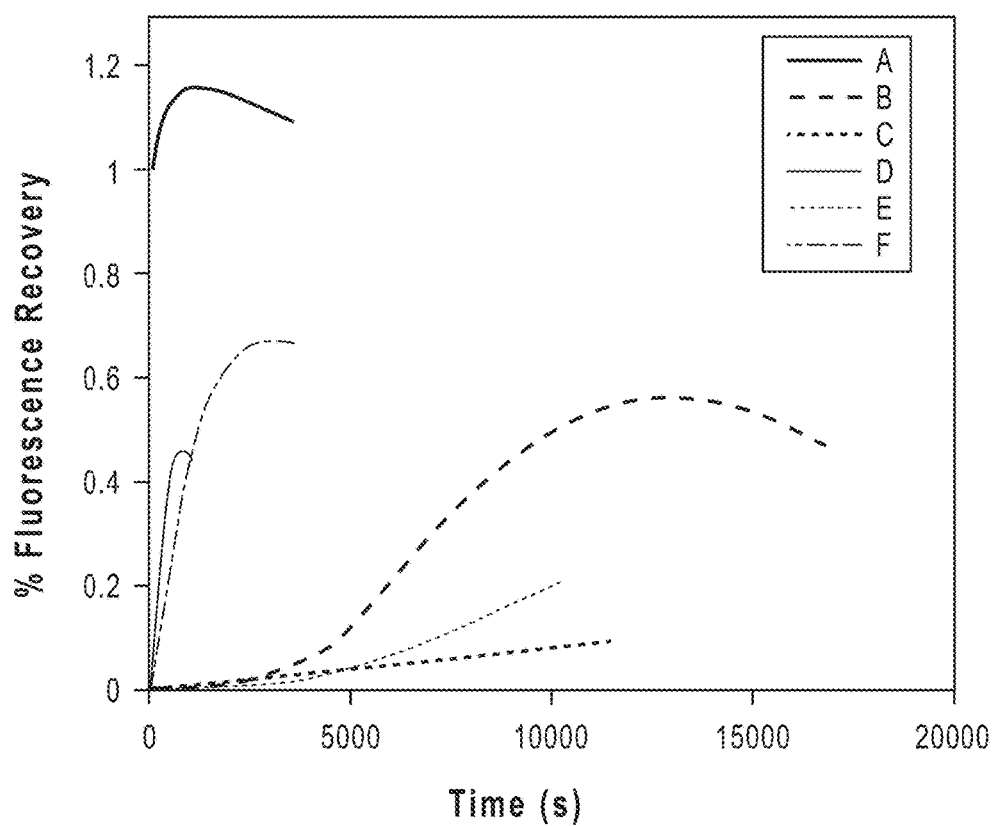
FIG. 7 is a plot showing the fluorescence recovery of nanocrystals with and without cyanide treatment.

Laser illumination (at 405 nm) was used to activate the fluorescence of copper-quenched nanocrystals. Hydrophilic nanocrystals were prepared as described in Example 2 using a combination of amphiphilic and PEG polymers. The nanocrystals were activated in buffer at pH 7.8 or 10 with and without cyanide treatment. FIG. 7 shows the fluorogenic response for the various materials tested: A) non-quenched fluorescent nanocrystals with illumination (control); B) quenched (pH 10 with illumination); C) quenched (pH 10, 2 mM KCN); D) quenched (pH 10, with illumination, 2 mM KCN); E) quenched (pH 7.8, with illumination); and F) quenched (pH 7.8 with illumination, 2 mM KCN). The data demonstrates that irradiation can restore the fluorescence emission intensity of quenched nanocrystals. Further, activation be dramatically enhanced and accelerated by irradiating the nanocrystals in conjunction with cyanide activation.

Example 5

Enzymatic Activation of Quenched Semiconductor Nanocrystals

Selective generation of the activators for restoring the fluorescence of quenched fluorogenic nanocrystals can be accomplished using catalytic (e.g., enzymatic), chemical, and photochemical approaches. Once nanocrystal fluorescence emission is restored, these nanocrystals can be used to detect a wide variety of analytes (e.g., proteins, oligonucleotides, small molecules, and the like) using many types of different assays.

Enzymatic activation of nanocrystal fluorescence can be demonstrated in a multi-well plate. Each well of the multi-well plate contains 1 to 50 nM copper-quenched QDOT 585 or QDOT 625 nanocrystals (prepared, for example, as described in Example 1), 10 to 200 mM cyanogenic substrate (e.g., amygdalin or prunasin) and 0 to 10 μM β-glucosidase in a 10 to 300 mM buffer pH 6 to 9 (e.g., MES, ACES, MOPS, HEPES, or Tris, CHES). The final volume of solution in each well can range from about 10 to 300 μL. All components are added to each well with the enzyme added last to initiate fluorescence recovery. Assays can be run at temperatures ranging from about 15 to about 60° C. Activation and readout can be carried out at the same or different temperatures and/or acidity depending on the constraints of the assay. Assays can be read out on various types of instruments, such as a fluorescence reader (e.g. M1000 plate reader from Tecan Group Ltd. (Switzerland) or a qPCR device, such as the StepOnePlus™ Real-Time PCR System from Applied Biosystems (Foster City, Calif.).

Example 6

Figure 8:
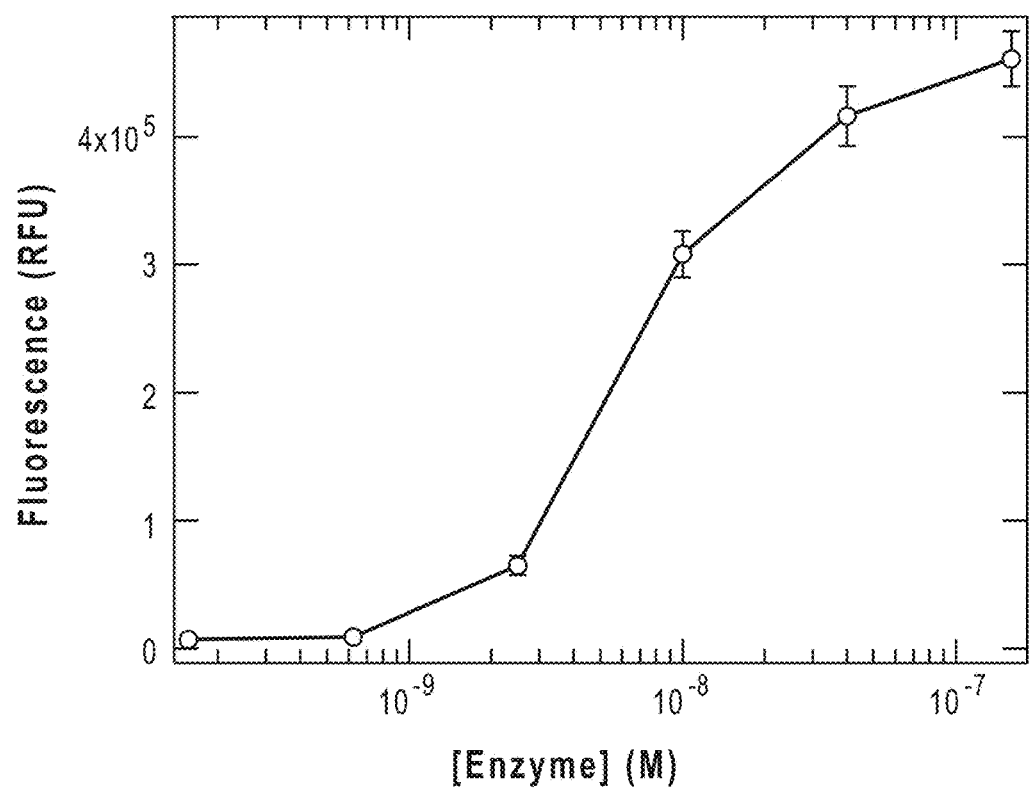
FIG. 8 is a titration curve for nanocrystals activated in the presence of a cyanogenic enzyme and substrate.

Two-Step Cyanogenic Enzyme Activation of Quenched Semiconductor Nanocrystals QDOT 625 nanocrystals (Life Technologies Corporation) were quenched as described in Example 1 or Example 2 and activated with cyanide generated by hydrolysis of amygdalin in the presence of glucosidase. Almond β-glucosidase (Sigma; St. Louis, Mo.) was titrated into a series of samples, each containing amygdalin (Sigma) (100 mM). The enzyme, nanocrystals and substrate were incubated at pH 6-8 for 0-3 hours. After incubation, the solutions were cooled on ice, and nanocrystals in basic buffer were added making the solution pH 10. This simultaneously initiated nanocrystal activation and halted enzyme activity. Fluorescence emission of the nanocrystals was measured over time using a StepOnePlus™ Real-Time PCR System (Life Technologies Corporation). The end-point titration curve shown in FIG. 8 shows that activation of the fluorogenic nanocrystals occurred upon contact with cyanide generated by cyanogenic enzyme and substrate.

Example 7

Digital Detection of Chemically Switched Semiconductor Nanocrystals

Figure 9:
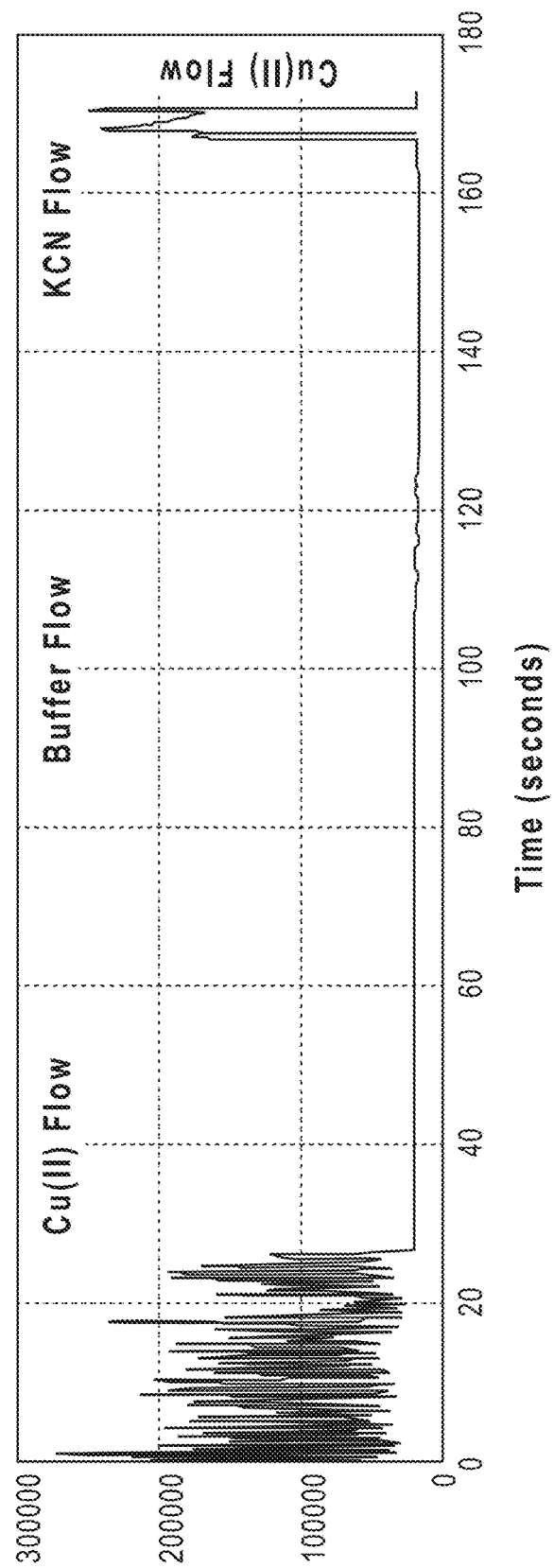
FIG. 9 is a plot showing the fluorescence response for a single nanocrystal in a chemical switching experiment.

This example describes chemical switching of nanocrystal fluorescence and digital detection at the single-molecule level using total internal reflectance fluorescence microscopy in a flow cell format. Surface-bound fluorogenic nanocrystals were washed alternately with solutions of quencher (e.g. a Cu(II) salt) and activator (e.g. KCN), while collecting images on a fluorescence microscope. A low density biotin surface (e.g., BIO-01 slides from MicroSurfaces, Inc. (Austin, Tex.) was treated with a 5 μM to 10 nM aqueous solution of QDOT 625 streptavidin nanocrystals (Life Technologies Corporation) to bind the nanocrystals to the slides. After a sufficient incubation period, unbound nanocrystals were washed away with a large volume of buffer, and then 100 nM to 10 μM of a Cu(II) solution was flowed over the surface to quench the fluorescence of remaining surface bound nanocrystals. A second wash removed excess Cu(II) ions. The quenched nanocrystals were activated by treatment with 100 μM to 100 mM KCN. After activation, excess KCN was washed from the nanocrystals, and fluorescence emission with 405 nm excitation was detected (FIG. 9).

Example 8

Digital Detection of Chemically Switched Semiconductor Nanocrystals

Figure 10A:
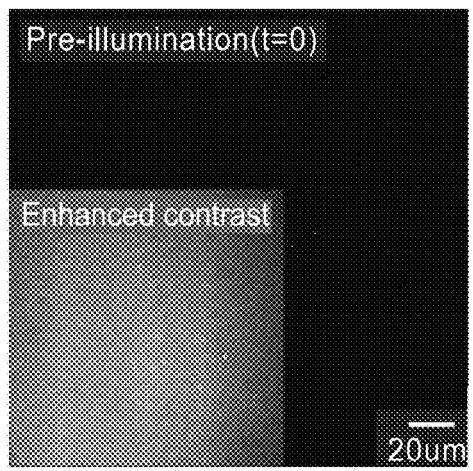
FIG. 10 shows images of single nanocrystals before (A) and after (B) photoactivation.
Figure 10B:
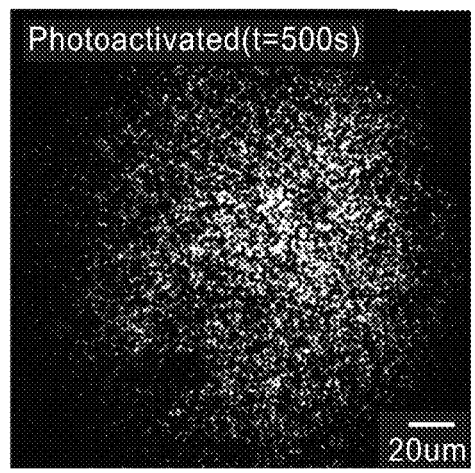
Figure 11:
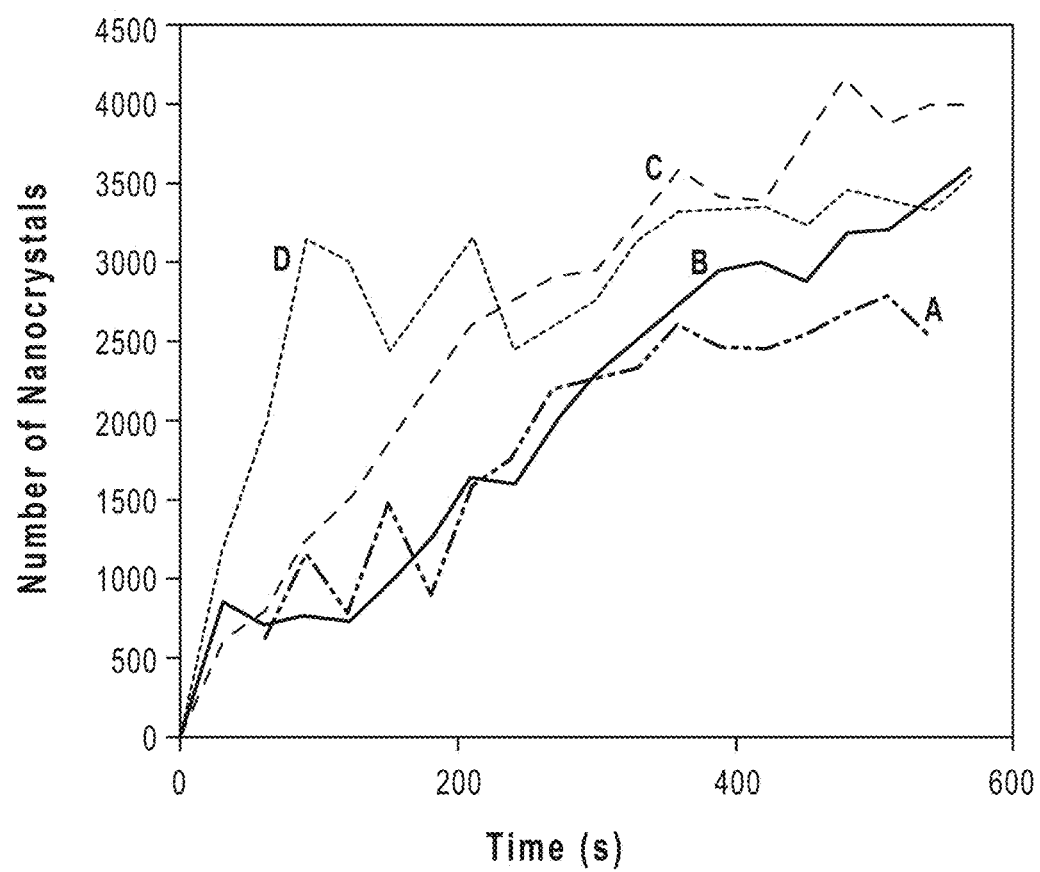
FIG. 11 is a plot comparing fluorescence response of nanocrystals with irradiation using (A) 20 W/cm$^2$; (B) 40 W/cm$^2$; (C) 80 W/cm$^2$; and (D) 20 W/cm$^2$ and 2 mM KCN.

This example describes photoactivation of nanocrystal fluorescence and digital detection at the single-molecule level using fluorescence microscopy in a flow cell format. Surface-bound fluorogenic nanocrystals were illuminated with a 405 nm laser while collecting fluorescence images on a fluorescence microscope. A low density biotin surface was prepared and treated as described in Example 7. After a sufficient incubation period, unbound nanocrystals were washed away with a large volume of buffer. A region of interest was illuminated at moderate power (1 to 100 $W/cm^2$) while imaging. FIG. 10 shows the quenched nanocrystals before (A) and (B) after illumination at a power of ~20 $mW/cm^2$. The fluorescence response of the photoactivated nanocrystals using irradiation at powers of 20 $W/cm^2$ to 80 $W/cm^2$ is shown in FIG. 11. The addition of KCN (10 μM to 100 mM) dramatically increased the rate of photoactivation of the quenched nanocrystals. The effect of irradiation (20 $W/cm^2$) in combination with 2 mM KCN treatment is plotted in FIG. 11 (D).

Example 9

Enhancement of Quantum Yield

Figure 12:
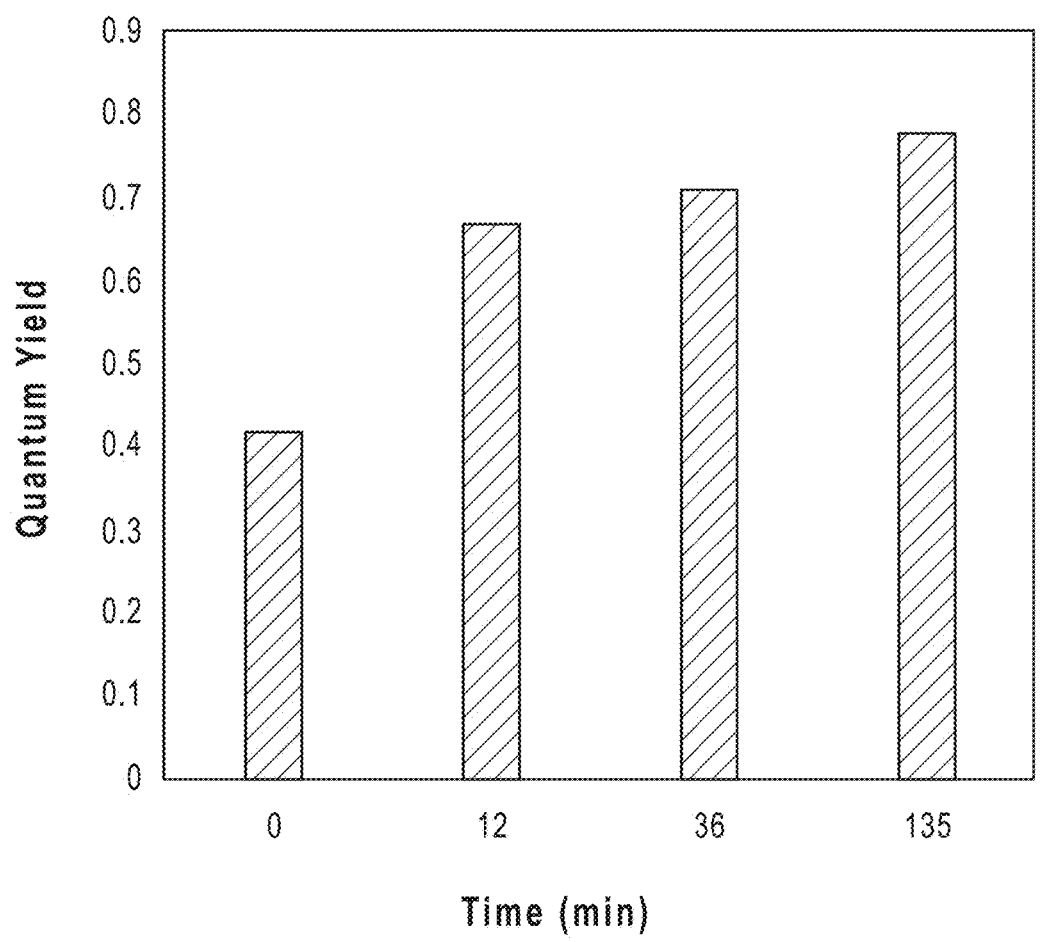
FIG. 12 is a bar graph showing the enhancement of quantum yield of fluorogenic nanocrystals upon illumination and cyanide treatment.

The effect of treating hydrophilic, semiconductor nanocrystals with cyanide under different reaction conditions is described. Thiol-coated nanocrystals were dispersed in aqueous buffer (pH 7.5, 50 mM Tris, 4 mM NaCl). 0.5 M KCN in water was added to the nanocrystal dispersion to provide a 143 mM KCN solution, and the reaction mixture was incubated. The quantum yield of the nanocrystals was measured after various time points. FIG. 12 shows a plot of quantum yield before treatment (A) and after incubation with cyanide for (B) 12 minutes; (C) 36 minutes; and (D) 135 minutes. The data demonstrate that quantum yield of fluorescent nanocrystals can be enhanced dramatically by treatment with a cyanide source.

Example 10

Optical Detection of Fluorogenic Nanocrystals in Live Cells

Live HeLa cells were encoded with fluorogenic nanocrystals, and photoactivation was used to rejuvenate fluorescence of the fluorogenic nanocrystals in the live cells. A labeling solution was made by mixing 1-8 μM hydrophilic, copper-quenched nanocrystals, prepared as described in Example 2, with an emission maximum of 625 nm and 1-3 mL of fresh growth medium or 1×HBSS (Life Technologies Corporation). The growth medium included GIBCO minimum essential medium (MEM) (Life Technologies Corporation) and 10% FBS (Life Technologies Corporation). The labeling solution was added to a monolayer of HeLa cells subcultured overnight in a 35 mm glass bottom dish. After incubation at 37° C. in a humidified atmosphere of 95% air, 5% $CO_2$ for 45-120 minutes, the cells were washed twice with fresh growth medium (containing MEM and 10% FBS) or buffer (e.g. 1×PBS or 1×HBSS).

Figure 13:
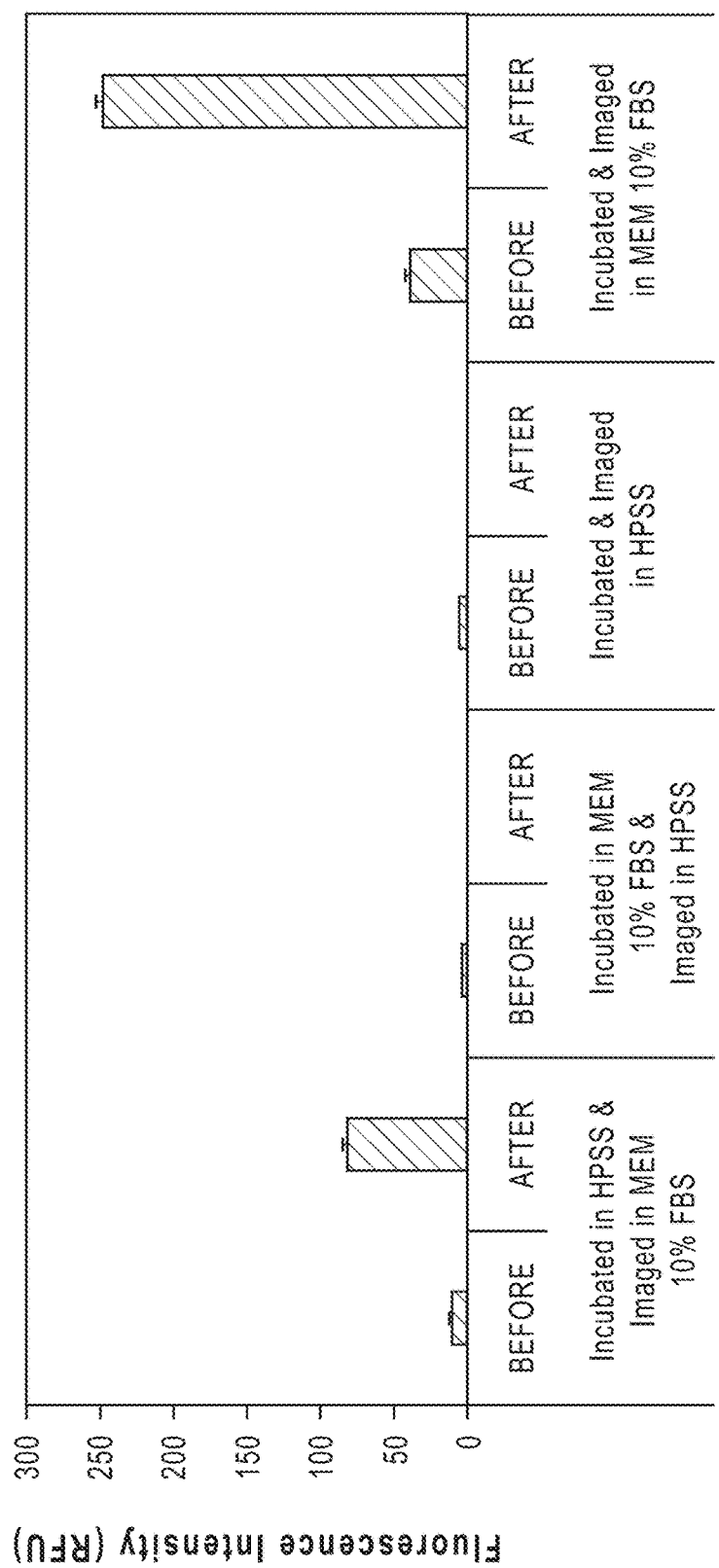
FIG. 13 is a bar graph comparing the fluorogenic response for copper-quenched nanocrystal samples incubated or imaged in HPSS or MEM and FBS (10%).

Laser illumination (at 405 nm or 458 nm) was used to activate the fluorescence of copper-quenched nanocrystals using a confocal microscope in whole cells or regions of cells. Fluorescence intensity was measured before activation (i.e., just after the illumination commenced) and after a period of prolonged illumination (~7 minutes). FIG. 13 shows fluorescence data collected for samples incubated or imaged in either HPSS or growth media. The results show that the fluorogenic response was most enhanced for nanocrystals imaged in the presence of MEM and 10% FBS.

Example 11

Activation and Detection of Fluorogenic Nanocrystals in Solution

Copper-quenched nanocrystals were photoactivated and imaged in a 96-well plate in real time using LED's (UV VCC Standard from Mouser Electronics). A labeling solution was made by mixing 1-8 μM hydrophilic, copper-quenched nanocrystals, prepared as described in Example 2, with an emission maximum of 625 nm and 1-3 mL of GIBCO minimum essential growth medium (60% MEM) and/or 20% FBS. All the samples contained either 50 mM MES or HEPES buffer and were at pH 6-8.

Figure 14:
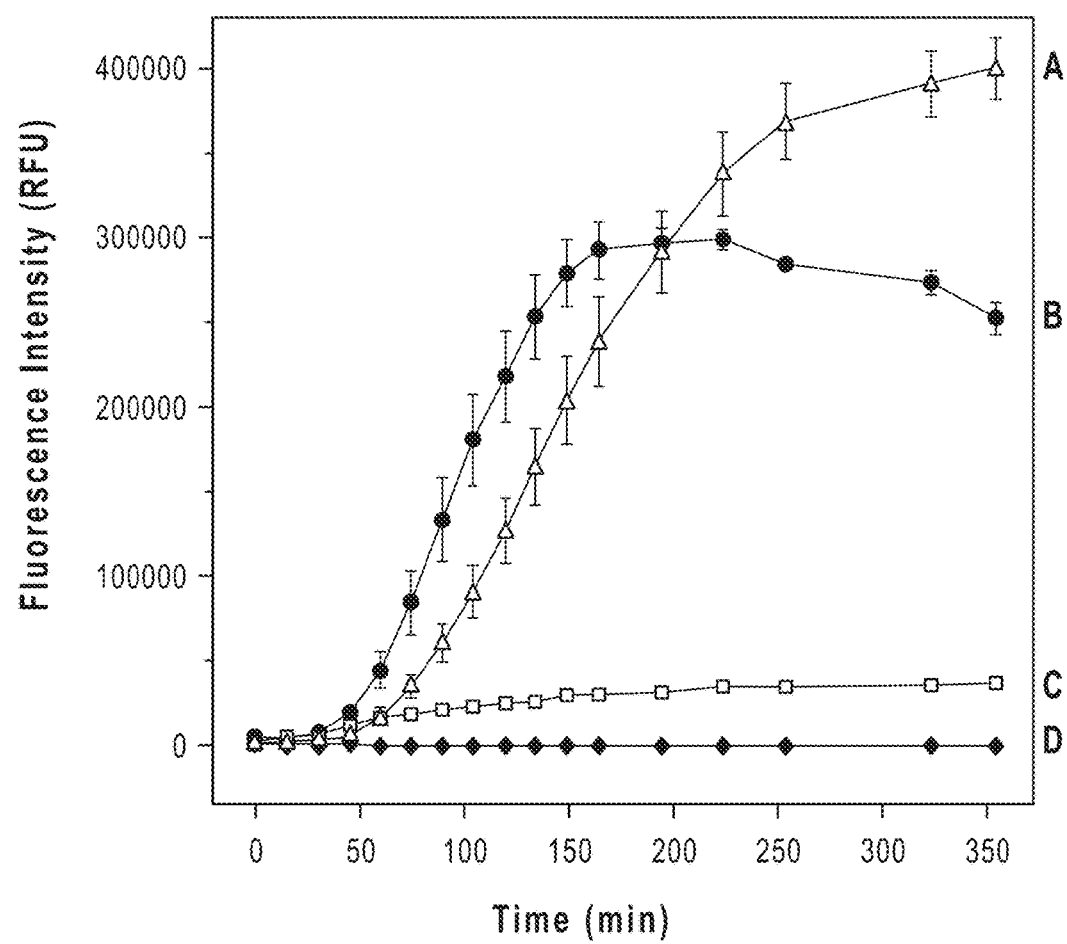
FIG. 14 is a plot showing the fluorogenic response of copper-quenched nanocrystals for samples activated and imaged in (A) FBS (20%); (B) MEM (60%) and FBS (20%); (C) MEM (60%); or (D) buffer alone.

FIG. 14 shows the fluorogenic response over time for samples activated and imaged in (A) FBS (20%); (B) MEM (60%) and FBS (20%); (C) MEM (60%); or (D) buffer alone. The photoactivation kinetics and end-point fluorescence of the quenched nanocrystals was significantly enhanced in the presence of FBS. Enhancement also was obtained when this experiment was performed using polyethyleneimine or BSA.

Example 12

Mandelonitrile Activation of Quenched Semiconductor Nanocrystals

Figure 15:
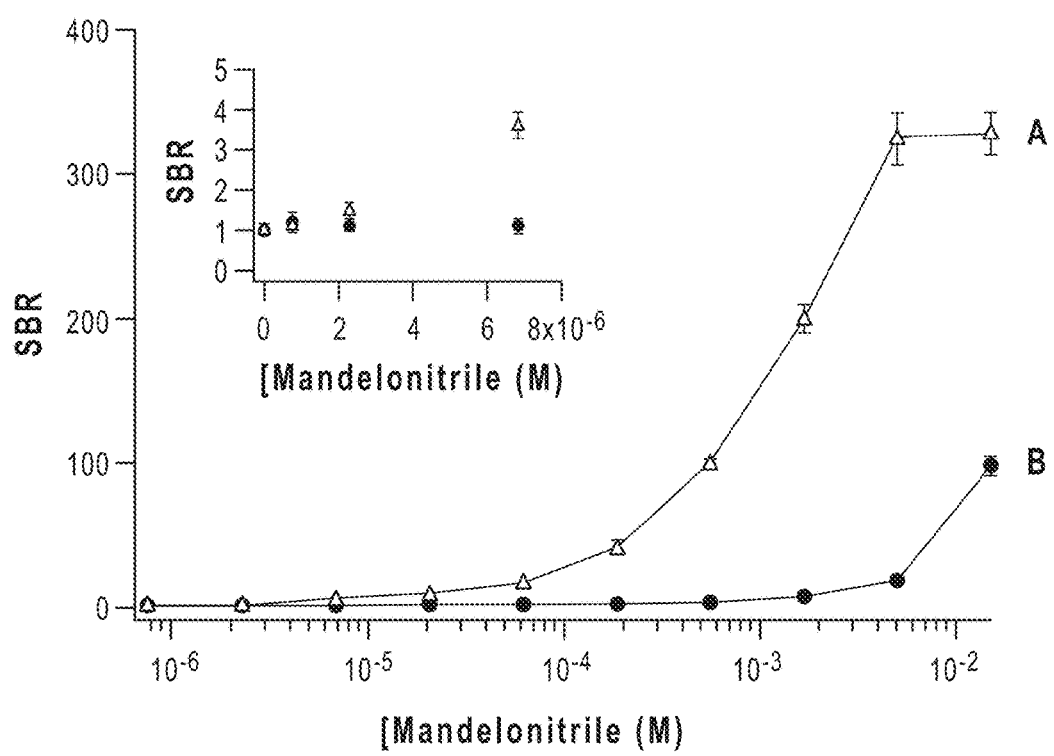
FIG. 15 is a plot showing the fluorogenic response at different mandelonitrile concentrations of fluorogenic nanocrystals with (A) and without (B) LED illumination as a function of mandelonitrile concentration.

A mandelonitrile dilution series was prepared in 100 mM MES, pH 6.0. The dilution series spanned a mandelonitrile concentration range from 40 mM to 0.68 μM and was compared to a buffer-only control reaction. Copper-quenched, core-shell semiconductor nanocrystals, prepared as described herein (20 nM in 1 M CHES, pH 10.0) were added to mandelonitrile dilutions at a final concentration of 4 nM. Reactions were mixed and centrifuged at 1000×g for one minute. One set of activation reactions was illuminated with 405 nm LEDs for fifteen minutes at room temperature. A second set of reactions proceeded in the absence of any illumination and protected from light for fifteen minutes. Nanocrystal fluorescence (405 nm excitation/625 nm emission) was detected after activation experiments. The fluorogenic response of the copper-quenched nanocrystals with (A) and without (B) LED illumination as a function of mandelonitrile concentration is shown in FIG. 15.

Example 13

Conjugation and Purification of AbG-Streptavidin for ELISA

β-Glucosidase (AbG) from almonds (Sigma-Aldrich Co., St. Louis, Mo.) was dissolved in 50 mM MOPS, pH 7.0 and 100 mM NaCl to a final concentration of 25 mg/mL. This solution was loaded onto a SUPERDEX 200 (GE HealthCare Bio-Sciences, AB, Sweden) size exclusion column equilibrated with 50 mM MOPS, pH 7.0 and 100 mM NaCl at 4° C. Elution fractions (1.5 mL each) were screened for p-nitrophenyl-β-D-glucopyranoside (pNPbG) hydrolysis. Fractions positive for hydrolysis were resolved by SDS-PAGE and those containing pure AbG were pooled. For streptavidin (SA) labeling, 0.5 mg AbG was combined with a ten-fold molar excess of $SM(PEG)_{24}$ crosslinker (Thermo Scientific, Rockford, Ill.) (dissolved in dry DMSO) in 100 mM sodium phosphate, pH 7.0. Meanwhile, 1 mg SA was reacted with a ten-fold molar excess of Traut's reagent (dissolved in dry DMSO) in 100 mM sodium phosphate, pH 7.0. Both reactions were incubated at room temperature for thirty minutes with shaking after which AbG-$PEG_{24}$-maleimide and SA-SH were isolated using P30 desalting spin columns (BIO-SPIN 30 columns from Bio-Rad Laboratories) equilibrated with 100 mM sodium phosphate, pH 7.0 and 5 mM EDTA. AbG-$PEG_{24}$-maleimide and SA-SH from the above reactions were combined and incubated at room temperature with shaking for two hours. AbG-$PEG_{24}$-SA conjugates were isolated using P30 desalting spin columns equilibrated with a solution of 50 mM MOPS, pH 7.0 and 100 mM NaCl. Conjugation was verified by SDS-PAGE resolution. Conjugates were purified from free streptavidin by size exclusion on a SUPERDEX 200 column. Column fractions were screened for biotin binding using biotin-coated 96-well plates (Thermo Scientific). Bound and soluble material from the plate binding assay was screened for pNPbG hydrolysis activity. Size exclusion fractions that contained hydrolysis activity in the bound phase, but not in the soluble phase were pooled and used for ELISA.

Example 14

Copper-Quenched Semiconductor Nanocrystals and AbG-SA IL-6 ELISA

Figure 16:
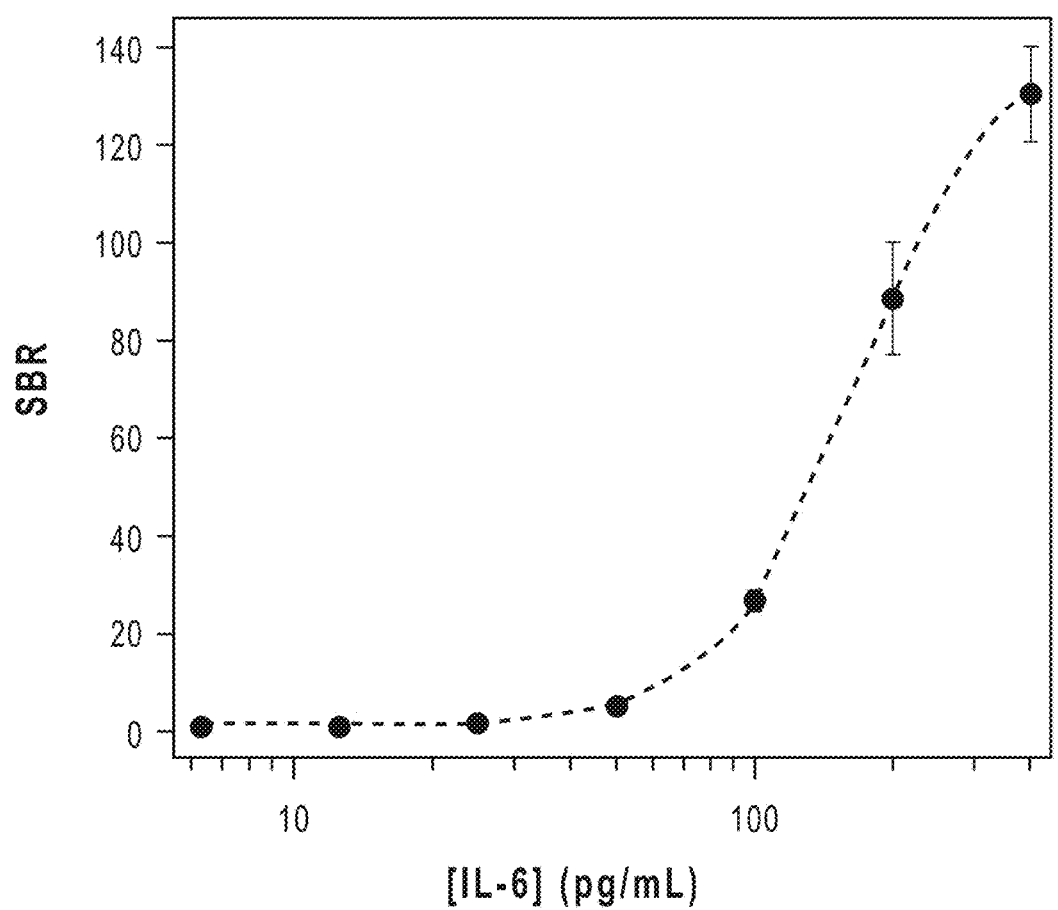
FIG. 16 is a plot showing the fluorogenic response of copper-quenched nanocrystals as a function of IL-6 concentration.

ELISA experiments were performed using the Human IL-6 UltraSensitive ELISA kit (KHC0064C; Life Technologies, Carlsbad, Calif.). A two-fold IL-6 dilution series was prepared covering a concentration range from 400 pg/mL to 6.25 pg/mL. IL-6-containing reactions were compared to a buffer only (no IL-6) negative control. Replicates (N=6) were prepared for each IL-6 titration point. Anti-IL-6 immunocomplexes were built following the manufacturer's protocol. For IL-6 detection, AbG-$PEG_{24}$-SA conjugate was added in place of the horse radish peroxidase streptavidin conjugate (HRP-SA) from the ELISA kit. AbG-$PEG_{24}$-SA (10 pmole, 830 ng per well) conjugate was incubated with immunocomplexes for forty-five minutes at room temperature on an orbital shaker. Supernatant was removed and unbound AbG-$PEG_{24}$-SA was washed away by rinsing each well six times with 0.4 mL of ELISA kit wash buffer. Amygdalin hydrolysis reactions were carried out in the ELISA plate wells by adding a solution (50 µL) of 100 mM amygdalin (Sigma-Aldrich) in 50 mM MES, pH 5.5 and incubating at 50° C. with shaking for two hours. After two hours, 16 µL of each hydrolysis reaction was transferred to a new 96-well plate and combined with a solution (4 µL) of 20 nM hydrophilic, copper-quenched nanocrystals (4 nM final concentration) prepared as in Example 2 (with PEG coating) in 1 M CHES, pH 10.0 (200 mM final concentration). The plate was sealed with optical adhesive film and the activation reactions were irradiated with 405 nm LEDs for thirty minutes at 4° C. Nanocrystal fluorescence (405 nm excitation/625 nm emission) was detected after activation. The fluorogenic response of the nanocrystals as a function of IL-6 concentration is shown in FIG. 16.

The foregoing examples illustrate various aspects of the invention and practice of the methods of the invention. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the following clauses and appended claims.

Embodiments may be in accordance with following numbered clauses:

1. A fluorogenic semiconductor nanocrystal, comprising:
a fluorescent semiconductor nanocrystal: and
a quencher group associated with the semiconductor nanocrystal, wherein the fluorescent semiconductor nanocrystal in the absence of the quencher group has an initial fluorescence intensity ($F_0$), and the fluorogenic semiconductor nanocrystal has a quenched fluorescence intensity ($F_Q$), wherein $F_Q/F_0$ is less than about 1.0.
2. The nanocrystal of clause 1, wherein the fluorogenic semiconductor nanocrystal is substantially non-emissive.
3. The nanocrystal of clause 1 or 2, wherein greater than 50 quencher groups are associated with the nanocrystal.
4. The nanocrystal of clause 1, 2 or 3, wherein the quencher group is or comprises a metal source.
5. The nanocrystal of clause 1, 2 or 3, wherein the quencher group is or comprises a transition or non-transition metal ion.
6. The nanocrystal of clause 1, 2 or 3, wherein the quencher group is or comprises a metal ion selected from Cu(I), Cu(II), Ag (I), Hg (I,II), Pb (II), Pb(IV), Fe (II), Fe(III), Co (II), Ni (II), and Cr (I, II, III, IV, V, or VI).
7. The nanocrystal of clause 1, 2 or 3, wherein the quencher group is or comprises an anion selected from $S^{2-}$, $Se^{2-}$, $F^-$, $Cl^-$, $Br^-$, $I^-$, $Te^{2-}$, or $As^{3-}$, and phosphonate; or an organic ligand comprising a thiol or thiolate group.
8. The nanocrystal of any one of the preceding clauses, further comprising a hydrophilic layer on the surface of the semiconductor nanocrystal that renders the nanocrystal water-dispersible.
9. The nanocrystal of any one of the preceding clauses, further comprising a biomolecule linked to the semiconductor nanocrystal or hydrophilic layer, wherein the biomolecule is selected from a nucleotide, an oligonucleotide, a nucleic acid polymer, an amino acid, polypeptide, a protein, a polysaccharide, a lipid, and biotin.
10. The nanocrystal of any one of the preceding clauses, wherein the nanocrystal comprises a semiconductor core and an external semiconductor shell layer disposed on the semiconductor core.
11. A population of nanocrystals, comprising a plurality of fluorogenic semiconductor nanocrystals according to any one of the preceding clauses.
12. A composition, comprising:
a population of fluorogenic semiconductor nanocrystals of clause 11; and
an aqueous or organic medium or a solid support, wherein the nanocrystal is associated with the support, if present.
13. A method for producing a fluorogenic nanocrystal, comprising:
a) providing a reaction mixture including a fluorescent semiconductor nanocrystal and at least one solvent; and b) adding to the reaction mixture a quencher group in an amount sufficient to reduce the fluorescence emission of the semiconductor nanocrystal.

14. The method of clause 13, wherein a plurality of quencher groups is added to the reaction mixture.

15. The method of clause 13 or 14, wherein the fluorescence emission signal is reduced by at least 50% upon addition of the quencher group.

16. The method of clause 14 or 15, wherein about $10^{-8}$ M to about $10^{-3}$ M of quencher groups is present in the reaction mixture.

17. The method of any one of the preceding clauses wherein greater than 50 quencher groups per nanocrystal are added to the reaction mixture.

18. The method of any one of the preceding clauses, wherein the quencher group is or comprises a metal source.

19. The method of any one of the preceding clauses, wherein the quencher group is or comprises a transition or non-transition metal ion.

20. The method of any one of the preceding clauses, wherein the quencher group is or comprises a metal ion selected from Cu(I), Cu(II), Ag (I), Hg (I,II), Pb (II), Pb(IV), Fe (II), Fe(III), Co (II), Ni (II), and Cr (I, II, III, IV, V, or VI); or an anion selected from $S^{2-}$, $Se^{2-}$, $F^-$, $Cl^-$, $Br^-$, $I^-$, $Te^{2-}$, or $As^{2-}$, and phosphonate; or an organic ligand comprising a thiol or thiolate group.

21. The method of any one of the preceding clauses, wherein the fluorescent semiconductor nanocrystals are water-dispersible.

22. The method of any one of the preceding clauses, further comprising treating the semiconductor nanocrystal after addition of the quenching group with a hydrophilic compound that renders the nanocrystal water-dispersible.

23. The method of any one of the preceding clauses, further comprising attaching to the nanocrystal an organic molecule (e.g., biomolecule).

24. A population of fluorogenic nanocrystals produced according to any one of the preceding methods.

25. A method of activating a fluorogenic semiconductor nanocrystal, comprising:
a) providing a fluorogenic semiconductor nanocrystal of any one of clauses 1 to 10;
b) contacting the nanocrystal with an activator, wherein the fluorescence intensity of the fluorogenic semiconductor nanocrystal after contact with the activator increases.

26. The method of clause 25, wherein the nanocrystal after contact with the activator has an activated fluorescence intensity ($F_A$), wherein $F_A/F_Q$ is greater than 1.

27. The method of clause 25 or 26, wherein the $F_A/F_Q$ is 10 or greater.

28. The method of clause 25, 26 or 27, wherein the activator is a reducing agent, oxidizing agent, proton, or metal ion binding compound.

29. The method of clause 25, 26 or 27, wherein the activator is selected from cyanide, nitrile, isonitrile, azide, thiocyanate, amine, imidazole, thiolate, carboxylate, NO, CO, halides, peroxide, ROS, and hydroxide.

30. The method of clause 25, 26 or 27, wherein the activator comprises a cyanide, isonitrile or nitrile source.

31. The method of clause 25, 26 or 27, wherein the activator is a cyanide ion, a cyanide salt or an organocyanide.

32. The method of clause 25, 26 or 27, further comprising contacting the nanocrystal with a cyanogenic substrate capable of releasing an isonitrile or a cyanide group.

33. The method of clause 32, further comprising hydrolyzing the substrate to release a cyanide ion.

34. The method of clause 32 or 33, wherein the substrate is a cyanogenic enzyme substrate.

35. The method of clause 32, 33 or 34, wherein the substrate is selected from amygdalin, prunasin, dhurrin, vicianin, linamarin, lotaustralin, cyanohydrins, cyanohydrin esters, cyanohydrin amides, acetone cyanohydrins, mandelonitrile, and acyl cyanides.

36. The method of clause 34 or 35, further comprising contacting the cyanogenic substrate with a cyanogenic enzyme capable of cleaving the cyanogenic substrate to release a compound comprising an isonitrile group or a cyanide group.

37. The method of clause 35 or 36, wherein the cyanogenic enzyme is a glucosidase.

38. The method of clause 35 or 36, wherein the cyanogenic enzyme is selected from almond β-glucosidase, amygdalase, and linamarase.

39. The method of clause 34, 35, 36 or 37, further comprising contacting the cyanogenic enzyme substrate with a lysase, esterase, protease, or galactase.

40. The method of any one of the preceding clauses, further comprising contacting the fluorogenic nanocrystal with a metal chelator.

41. A population of activated fluorogenic nanocrystals produced according to the method of any one of clauses 25 to 40.

42. A method of detecting the presence of a target analyte in a sample, comprising:
a) providing a cyanogenic substrate capable of releasing a cyanide source;
b) contacting the sample with a fluorogenic semiconductor nanocrystal according to any one of clauses 1 to 10, wherein the nanocrystal is associated with a first binding group;
c) contacting the sample with a second binding group, wherein the second binding group is associated with a cyanogenic enzyme, wherein the first and second binding groups are different, and wherein the first and second binding groups bind to the analyte, if present;
d) contacting the cyanogenic enzyme with the cyanogenic substrate, thereby releasing the cyanide source from the cyanogenic substrate; and
e) detecting fluorescence emission of the fluorogenic semiconductor nanocrystal, wherein an increase in the intensity of fluorescence emission signal indicates the presence of the analyte in the sample.

43. A method of detecting the presence of an analyte in a sample, comprising:
a) providing i) a cyanogenic substrate that is capable of releasing a cyanide source and ii) a fluorogenic nanocrystal according to any one of clauses 1 to 10;
b) contacting the sample with a binding group and a second binding group, wherein the first binding group and the second binding group are different, wherein the first and second binding groups bind to the analyte, if present, wherein the first binding group is associated with a cyanogenic enzyme;
c) contacting the cyanogenic enzyme with the cyanogenic substrate to release the cyanide source in the presence of the nanocrystal; and
d) detecting fluorescence emission of the fluorogenic semiconductor nanocrystal, wherein an increase in the intensity of fluorescence emission signal indicates the presence of the analyte in the sample.

44. The method of clause 43, wherein the first binding group is associated with a third binding group, wherein the third binding group is associated with the cyanogenic enzyme.

45. A method of detecting the presence of an analyte in a sample, comprising:
a) providing a solid support, wherein the support is associated with a first binding group and a cyanogenic enzyme;
b) contacting the solid support with the sample and a second binding group wherein the first and second binding group binds to the analyte, if present, wherein the second binding group is associated with the fluorogenic semiconductor nanocrystal according to any one of clauses 1 to 10, and wherein the first and second binding groups are different;
c) contacting the cyanogenic enzyme with a cyanogenic substrate to release a cyanide source; and
d) detecting fluorescence emission of the fluorogenic semiconductor nanocrystal, wherein an increase in the intensity of fluorescence emission signal indicates the presence of the analyte in the sample.

46. The method of any one of clauses 42-45, wherein the first and/or second is selected from an antibody, oligonucleotide, aptamer, and chemical binding group (e.g., polymers, metal ligands, protein binding chemicals, activity probes).

47. The method of any one of clauses 42-45, wherein the first binding group is associated with a solid support, and, optionally, further comprising washing the solid support before addition of the cyanogenic substrate.

48. The method of any one of clauses 42-45, wherein the analyte is a biomolecule, cell, or a small inorganic or organic molecule.

49. A method of detecting the presence of a nucleic acid in a sample, comprising:
a) contacting a sample with a fluorogenic semiconductor nanocrystal according to any one of clauses 1 to 10, wherein the nanocrystal is associated with a first nucleic acid having a known sequence;
b) contacting the sample with a second nucleic acid having a known sequence, wherein the second nucleic acid is associated with a cyanogenic enzyme;
c) contacting the cyanogenic enzyme with the cyanogenic substrate, thereby releasing a cyanide source (e.g., cyanide ion or isonitrile group) from the cyanogenic substrate; and
e) detecting the fluorescence emission of the fluorogenic semiconductor nanocrystal, wherein an increase in the intensity of fluorescence emission signal indicates the presence of a nucleic acid strand having a sequence capable of hybridizing to the first and second nucleic acid strands.

50. A fluorogenic assay system, comprising:
a) a fluorogenic semiconductor nanocrystal according to any one of clauses 1 to 10, wherein the nanocrystal is associated with a first binding group;
b) a cyanogenic enzyme associated with a second binding group, wherein the second binding group is different from the binding group, and wherein the first and the second binding groups are associated with an analyte; and
c) a cyanogenic substrate capable of releasing a cyanide source (e.g., cyanide ion or an isonitrile group) upon contact with the cyanogenic enzyme.

51. The assay system of clause 50, wherein the cyanogenic enzyme and/or the second binding groups is associated with a solid support.

52. A method of activating a semiconductor nanocrystal, comprising:
a) providing at least one fluorescent semiconductor nanocrystal or fluorogenic nanocrystal according to any one of clauses 1 to 10;
b) contacting the semiconductor nanocrystal with a compound to modulate the at least one optical property of the nanocrystal; and
c) determining the position of the nanocrystal.

53. The method of clause 52, wherein the positions of a first nanocrystal and a second nanocrystal are determined to an accuracy that is less than the wavelength of the light emitted by first and/or second nanocrystal.

54. A method of detecting cyanide ions in a sample, comprising:
a) providing a sample;
b) contacting the sample with a fluorogenic semiconductor nanocrystal according to any one of clauses 1 to 10, wherein the quencher group is capable of complexing with a cyanide ion; and
c) detecting fluorescence emission of the nanocrystal, wherein an increase in the intensity of fluorescence emission signal indicates the presence of the cyanide ions in the sample.

55. A method of enhancing the brightness of a semiconductor nanocrystal, comprising:
a) providing a fluorescent semiconductor nanocrystal; and
b) contacting the nanocrystal with an activator, such that the intensity of the fluorescence emission of the population of nanocrystals increases by at least 10%.

56. The method of clause 55, wherein the activator comprises a cyanide source.

57. A method of attaching a compound to a semiconductor nanocrystal, comprising:
a) contacting a fluorescent semiconductor nanocrystal that comprises an alkyne reactive group or an azide reactive group;
b) contacting the nanocrystal with a reactive material comprising a group capable of reacting with the alkyne reactive group or azide reactive group of the compound in the presence of Cu(I) or Cu(II) ions; and
c) contacting the nanocrystal with an activator, wherein the fluorescence emission intensity of the nanocrystal increases upon contact with the activator.

58. A kit, comprising:
a) a population of fluorogenic nanocrystals according to clause 24; and
b) an activator.

59. A kit, comprising:
a) a population of fluorogenic nanocrystals according to clause 24;
b) a cyanogenic enzyme; and
b) a cyanogenic substrate.

60. A kit, comprising:
a) a population of fluorescent nanocrystals;
b) a copper source;
c) a cyanogenic enzyme; and
d) a cyanogenic substrate.

61. A kit, comprising:
a) a population of fluorescent semiconductor nanocrystals, wherein each semiconductor nanocrystal in the population comprises an alkyne reactive group or an azide reactive group;
b) a copper source; and
c) at least one activator.

62. A method of identifying a cell or cellular component in a sample, comprising:
a) contacting a cell or cellular component in the sample with a fluorogenic semiconductor nanocrystal according to any one of clauses 1 to 10 under conditions in which the nanocrystal is transported across the cell membrane to provide a labeled cell or cellular component;
b) exposing the labeled cell or cellular component to an excitation energy source to activate the semiconductor nanocrystal, such that the activated nanocrystal has a fluorescence intensity ($F_A$), wherein $F_A/F_Q$ is greater than 1; and c) detecting the fluorescence emission of the activated nanocrystal, thereby identifying the cell or cellular component in the sample.

63. A method of identifying a cell in a mixed population of cells, comprising:
a) contacting a first cell with a fluorogenic semiconductor nanocrystal according to any one of clauses 1 to 10 under conditions in which the nanocrystal is associated with the cell to provide a first labeled cell;
b) mixing the first labeled cell with a second cell distinct from the first cell to form a mixed population of cells;
c) culturing the mixed population of cells;
d) exposing the labeled cell to an excitation energy source to activate the semiconductor nanocrystal, such that the activated nanocrystal has a fluorescence intensity ($F_A$), wherein $F_A/F_Q$ is greater than 1; and
e) detecting the fluorescence emission of the activated nanocrystal, thereby identifying the first labeled cell in the mixed population of cells.

64. The method of clause 62 or 63, wherein the cell is a mammalian or yeast cell.

65. The method of clause 62, 63 or 64, wherein the cell a live cell.

66. The method of clause 62, 63, 64 or 65, further comprising contacting the labeled cell or cellular component to an activator prior to or during exposing the labeled cell or cellular component to the excitation energy source.

67. A method for detecting a fluorogenic nanocrystal, comprising:
a) placing a fluorogenic nanocrystal according to any one of clauses 1 to 10 onto the surface of a photonic crystal sensor;
b) illuminating the photonic crystal sensor with light, thereby causing the sensor to exhibit an extraction resonance mode having a spectrum which at least partially overlaps the emission spectrum of the fluorogenic nanocrystal, wherein the illumination and the extraction resonance mode activates the fluorogenic nanocrystal, such that the activated nanocrystal has a fluorescence intensity ($F_A$), wherein $F_A/F_Q$ is greater than 1; and
c) detecting the emitted light from the activated nanocrystal, thereby detecting the fluorogenic nanocrystal.

68. The method of clause 70, further comprising contacting the fluorogenic nanocrystal with an activator, thereby increasing the rate of activation and/or fluorescence intensity.

69. The method or kit of any one of the preceding clauses, wherein the activator is a polymer or protein.

70. The method or kit of any one of the preceding clauses, wherein the activator is fetal bovine serum, bovine serum albumin, casein, goat serum, or fish serum.

71. The method or kit of any one of the preceding clauses, wherein the activator is polyethyleneimine, polypeptide, polyethylene glycol, or polyacrylic acid or a derivative thereof.

72. The method or kit of any one of the preceding clauses, wherein the activator is a reducing agent, oxidizing agent, proton, or metal ion binding compound.

73. The method or kit of any one of the preceding clauses, wherein the activator is selected from cyanide, nitrile, isonitrile, azide, thiocyanate, amine, imidazole, thiolate, carboxylate, NO, CO, halides, peroxide, ROS, and hydroxide.

74. The method or kit of any one of the preceding clauses, wherein the activator comprises a cyanide, isonitrile or nitrile source.

75. The method or kit of any one of the preceding clauses, wherein the activator is a cyanide ion, a cyanide salt or an organocyanide.

76. Use of a fluorogenic semiconductor nanocrystal according to any one of the preceding clauses for identifying a cell or cellular component in a sample.

77. Use of a fluorogenic semiconductor nanocrystal according to any one of the preceding clauses in a biological assay or for detecting a target analyte in a sample.

78. Use of a fluorogenic semiconductor nanocrystal according to any one of the preceding clauses as a cyanide ion sensor.

What is claimed is:

1. A method of activating a fluorogenic semiconductor nanocrystal, comprising:
a) providing a water-dispersible fluorogenic semiconductor nanocrystal in an aqueous medium, the aqueous medium comprising:
a fluorescent semiconductor nanocrystal, wherein the nanocrystal comprises a semiconductor core, and an external semiconductor shell layer disposed on the semiconductor core;
a hydrophilic layer on the surface of the external semiconductor shell layer that renders the nanocrystal water-dispersible; and
a quencher group associated with the external semiconductor shell layer, wherein the quencher group is a copper ion, wherein the fluorescent semiconductor nanocrystal in the absence of the quencher group has an initial fluorescence intensity ($F_0$), and the fluorogenic semiconductor nanocrystal has a quenched fluorescence intensity ($F_Q$), wherein $F_Q/F_0$ is less than about 1.0; and
b) contacting the nanocrystal with an activator at a pH of greater than 7, wherein the activator comprises a cyanogenic enzyme substrate; and
c) contacting the cyanogenic enzyme substrate with a cyanogenic enzyme capable of cleaving the cyanogenic substrate to release a compound comprising a nitrile, an isonitrile or a cyanide group, wherein the fluorescence intensity of the fluorogenic semiconductor nanocrystal after contact with the activator increases, wherein the nanocrystal after contact with the activator has an activated fluorescence intensity ($F_A$), wherein $F_A/F_Q$ is 10 or greater.

2. The method of claim 1, wherein the cyanogenic enzyme substrate is selected from amygdalin, prunasin, dhurrin, vicianin, linamarin, lotaustralin, cyanohydrins, cyanohydrin esters, cyanohydrin amides, acetone cyanohydrins, mandelonitrile, and acyl cyanides.

3. The method of claim 1, wherein the cyanogenic enzyme is a glucosidase.

4. The method of claim 1, wherein the cyanogenic enzyme is selected from almond β-glucosidase, amygdalase, and linamarase.

5. The method of claim 1, further comprising illuminating the fluorogenic semiconductor nanocrystal with light.

6. The method of claim 1, wherein the semiconductor core comprises CdSe.

7. The method of claim 1, wherein the external semiconductor shell layer comprises a semiconductor material selected from Group II-VI, Group II-II-VI, and Group II-VI-VI semiconductor materials.

8. The method of claim 1, further comprising hydrolyzing the compound to release the isonitrile or cyanide group.

* * * * *